United States Patent [19]

Grainger et al.

[11] Patent Number: 5,847,007

[45] Date of Patent: *Dec. 8, 1998

[54] PREVENTION AND TREATMENT OF PATHOLOGIES ASSOCIATED WITH ABNORMALLY PROLIFERATIVE SMOOTH MUSCLE CELLS

[75] Inventors: David J. Grainger; James C. Metcalfe; Peter L. Weissberg, all of Cambridge, England

[73] Assignee: NeoRx Corporation, Seattle, Wash.

[ * ] Notice: The term of this patent shall not extend beyond the expiration date of Pat. No. 5,472,985.

[21] Appl. No.: 242,161

[22] Filed: May 12, 1994

Related U.S. Application Data

[63] Continuation-in-part of Ser. No. 61,714, May 13, 1993, abandoned.

[51] Int. Cl.⁶ .................................................. A61K 31/135
[52] U.S. Cl. .......................................... 514/651; 514/824
[58] Field of Search ............................... 514/56, 651, 824

[56] References Cited

U.S. PATENT DOCUMENTS

| | | | |
|---|---|---|---|
| Re. 32,944 | 6/1989 | Harita et al. | 562/455 |
| Re. 33,403 | 10/1990 | Stolle et al. | 424/87 |
| 2,914,563 | 11/1959 | Allen et al. | 260/570 |
| 3,010,965 | 11/1961 | Elpern | 260/293 |
| 3,168,565 | 2/1965 | Palopoli et al. | 260/570.7 |
| 3,288,806 | 11/1966 | DeWald et al. | 260/326.5 |
| 3,634,517 | 1/1972 | Palopodi et al. | 260/590 |
| 3,940,422 | 2/1976 | Harita et al. | 560/340 |
| 4,070,484 | 1/1978 | Harita et al. | 424/319 |
| 4,133,814 | 1/1979 | Jones et al. | 260/326 |
| 4,230,862 | 10/1980 | Suarez et al. | 546/237 |
| 4,235,988 | 11/1980 | Fildes et al. | 528/79 |
| 4,307,111 | 12/1981 | Crawley | 424/278 |
| 4,323,707 | 4/1982 | Suarez et al. | 564/324 |
| 4,380,635 | 4/1983 | Peters | 546/324 |
| 4,418,068 | 11/1983 | Jones | 424/267 |
| 4,442,119 | 4/1984 | Magarian et al. | 424/274 |
| 4,512,762 | 4/1985 | Spears | 604/21 |
| 4,536,516 | 8/1985 | Harper et al. | 514/514 |
| 4,696,949 | 9/1987 | Toivola et al. | 514/648 |
| 4,824,436 | 4/1989 | Wolinsky | 604/53 |
| 4,826,672 | 5/1989 | Milius et al. | 424/1 |
| 4,835,002 | 5/1989 | Wolf et al. | 426/590 |
| 4,839,155 | 6/1989 | McCague | 424/1 |
| 4,859,585 | 8/1989 | Sonnenschein et al. | 435/29 |
| 4,879,315 | 11/1989 | Magarian et al. | 514/754 |
| 4,929,602 | 5/1990 | Harker et al. | 514/18 |
| 4,962,091 | 10/1990 | Eppstein et al. | 514/2 |
| 4,973,755 | 11/1990 | Grafe et al. | 564/324 |
| 4,990,538 | 2/1991 | Harris et al. | 514/648 |
| 4,996,225 | 2/1991 | Tiovola et al. | 514/648 |
| 4,997,652 | 3/1991 | Wong | 424/428 |
| 5,015,666 | 5/1991 | Magarian et al. | 514/754 |
| 5,026,537 | 6/1991 | Dodonna | 424/1.1 |
| 5,032,679 | 7/1991 | Brandley et al. | 536/21 |
| 5,043,335 | 8/1991 | Kleinschroth et al. | 514/211 |
| 5,047,431 | 9/1991 | Schickaneder et al. | 514/648 |
| 5,049,132 | 9/1991 | Shaffer et al. | 604/101 |
| 5,053,033 | 10/1991 | Clarke | 606/3 |
| 5,075,321 | 12/1991 | Schreiber | 514/317 |
| 5,098,903 | 3/1992 | Magarian et al. | 514/255 |
| 5,112,305 | 5/1992 | Barath et al. | 604/96 |

(List continued on next page.)

FOREIGN PATENT DOCUMENTS

| | | |
|---|---|---|
| 0 095 875 | 12/1983 | European Pat. Off. . |
| 0 260 066 | 5/1990 | European Pat. Off. . |
| 0 365 863 B1 | 5/1990 | European Pat. Off. . |
| 0 374 044 B1 | 6/1990 | European Pat. Off. . |
| 0 451 202 B1 | 10/1991 | European Pat. Off. . |
| 0 542 679 A1 | 5/1993 | European Pat. Off. . |
| 0 584 953 A1 | 3/1994 | European Pat. Off. . |
| 0 588 518 A1 | 3/1994 | European Pat. Off. . |

(List continued on next page.)

OTHER PUBLICATIONS

Craig et al. "Modern Pharmacology", published 1982 by Little, Brown and Company (Boston), p. 399.
English language translation of WO 85/00107, Schulze et al., Jan. 85.
Avery's Drug Treatment, 3rd edition, pp. 594–595, 1987.
A. A. Colletta, et al., "Anti–oestrogens induce the secretion of active transforming growth factor beta from human fetal fibroblasts", *Br. J. Cancer*, 62, 405–409 (1990).
E. R. Edelman, et al., "Effect of controlled adventitial heparin delivery on smooth muscle cell proliferation following endothelial injury", *Proc. Natl. Acad. Sci. USA*, 87, 3773–3777 (May 1990).
D. J. Grainger, et al., "Effect of Tamoxifen in the Rat Carotid Injury Model in vivo," Manuscript in preparation (1996).
R. A. Majack, et al., "Role of PDGF–A Expresion in the Control of Vascular Smooth Muscle Cell Growth by Transforming Growth Factor–B", *The Journal of Cell Biology*, 111, 239–247 (1990).

(List continued on next page.)

Primary Examiner—Raymond Henley, III
Attorney, Agent, or Firm—Schwegman, Lundberg, Woessner & Kluth, P.A.

[57] ABSTRACT

TGF-beta activators and TGF-beta production stimulators are employed to maintain or increase vessel lumen diameter in a diseased or injured vessel of a mammal. Conditions such as restenosis following angioplasty, vascular bypass grafts, transplanted organs, atherosclerosis or hypertension are characterized by a reduced vessel lumen diameter. In a preferred embodiment of the invention, TGF-beta activators and production stimulators inhibit abnormal proliferation of smooth muscle cells. TGF-beta activators or production stimulators that are not characterized by an undesirable systemic toxicity profile at a prophylactic dose are also amenable to chronic use for prophylactic purposes with respect to disease states involving proliferation and/or migration of vascular smooth muscle cells over time. Further provided is a method for determining TGF-beta in vitro, thereby identifying a patient at risk for atherosclerosis and monitoring a recipient that has received one or more administrations of a TGF-beta activator or production stimulator.

16 Claims, 2 Drawing Sheets

U.S. PATENT DOCUMENTS

| | | | |
|---|---|---|---|
| 5,116,864 | 5/1992 | March et al. | 514/455 |
| 5,120,535 | 6/1992 | Marquardt et al. | 424/85.5 |
| 5,140,012 | 8/1992 | McGovern et al. | 514/19 |
| 5,166,143 | 11/1992 | Ondetti et al. | 514/89 |
| 5,171,217 | 12/1992 | March et al. | 604/53 |
| 5,180,366 | 1/1993 | Woods et al. | 604/96 |
| 5,185,260 | 2/1993 | Crissman et al. | 435/244 |
| 5,189,046 | 2/1993 | Burch et al. | 514/330 |
| 5,189,212 | 2/1993 | Ruenitz | 562/468 |
| 5,192,525 | 3/1993 | Yang et al. | 424/1.1 |
| 5,208,019 | 5/1993 | Hansson et al. | 424/85 |
| 5,213,576 | 5/1993 | Abiuso et al. | 604/96 |
| 5,213,580 | 5/1993 | Slepian et al. | 623/1 |
| 5,216,126 | 6/1993 | Cox et al. | 530/350 |
| 5,219,548 | 6/1993 | Yang et al. | 424/1 |
| 5,221,620 | 6/1993 | Purchio et al. | 435/69 |
| 5,226,430 | 7/1993 | Spears et al. | 128/898 |
| 5,238,714 | 8/1993 | Wallace et al. | 427/213 |
| 5,238,950 | 8/1993 | Clader et al. | 514/360 |
| 5,242,397 | 9/1993 | Barath et al. | 604/96 |
| 5,254,594 | 10/1993 | Niikura et al. | 514/648 |
| 5,268,358 | 12/1993 | Fretto et al. | 514/12 |
| 5,270,047 | 12/1993 | Kauffman et al. | 424/422 |
| 5,280,016 | 1/1994 | Conrad et al. | 514/56 |
| 5,280,109 | 1/1994 | Miyazono et al. | 530/399 |
| 5,283,257 | 2/1994 | Gregory et al. | 514/410 |
| 5,288,711 | 2/1994 | Mitchell et al. | 514/36 |
| 5,296,492 | 3/1994 | Shiozawa et al. | 514/337 |
| 5,304,541 | 4/1994 | Purchio et al. | 514/12 |
| 5,308,622 | 5/1994 | Casscells et al. | 424/422 |
| 5,308,862 | 5/1994 | Ohlstein | 514/411 |
| 5,316,766 | 5/1994 | Baldus et al. | 424/94 |
| 5,324,736 | 6/1994 | Magarian et al. | 514/317 |
| 5,326,757 | 7/1994 | Demopoulos | 514/167 |
| 5,328,471 | 7/1994 | Slepian | 604/101 |
| 5,340,925 | 8/1994 | Lioubin et al. | 530/395 |
| 5,346,993 | 9/1994 | Miyazono et al. | 530/399 |
| 5,354,562 | 10/1994 | Platz et al. | 424/489 |
| 5,354,774 | 10/1994 | Deckelbaum et al. | 514/455 |
| 5,354,801 | 10/1994 | O'Toole et al. | 524/461 |
| 5,362,424 | 11/1994 | Lee et al. | 264/4 |
| 5,364,632 | 11/1994 | Benita et al. | 424/450 |
| 5,380,716 | 1/1995 | Conrad et al. | 514/56 |
| 5,384,332 | 1/1995 | Fontana | 514/648 |
| 5,385,935 | 1/1995 | Tamai et al. | 514/535 |
| 5,389,670 | 2/1995 | Fontana | 514/443 |
| 5,391,557 | 2/1995 | Cullinan et al. | 514/324 |
| 5,393,763 | 2/1995 | Black et al. | 514/333 |
| 5,393,772 | 2/1995 | Yue et al. | 514/410 |
| 5,393,785 | 2/1995 | Labrie et al. | 514/622 |
| 5,395,842 | 3/1995 | Labrie et al. | 514/320 |
| 5,418,252 | 5/1995 | Williams | 514/443 |
| 5,426,123 | 6/1995 | Fontana | 514/651 |
| 5,436,243 | 7/1995 | Sachs et al. | 514/231 |
| 5,439,923 | 8/1995 | Cullinan | 514/324 |
| 5,439,931 | 8/1995 | Sales | 514/443 |
| 5,441,947 | 8/1995 | Dodge et al. | 514/179 |
| 5,441,964 | 8/1995 | Bryant et al. | 514/324 |
| 5,441,965 | 8/1995 | Sall et al. | 514/324 |
| 5,441,966 | 8/1995 | Dodge | 514/324 |
| 5,444,164 | 8/1995 | Purchio et al. | 536/23.5 |
| 5,445,941 | 8/1995 | Yang | 435/6 |
| 5,446,053 | 8/1995 | Keohane | 514/324 |
| 5,447,941 | 9/1995 | Zuckerman | 514/324 |
| 5,451,589 | 9/1995 | Dodge | 514/324 |
| 5,451,590 | 9/1995 | Dodge | 514/324 |
| 5,453,436 | 9/1995 | Ohlstein | 514/411 |
| 5,453,442 | 9/1995 | Bryant et al. | 514/408 |
| 5,455,275 | 10/1995 | Fontana | 514/648 |
| 5,457,116 | 10/1995 | Black et al. | 514/324 |
| 5,457,117 | 10/1995 | Black et al. | 514/337 |
| 5,461,064 | 10/1995 | Cullinan | 514/324 |
| 5,461,065 | 10/1995 | Black et al. | 514/324 |
| 5,462,937 | 10/1995 | Cullinan et al. | 514/212 |
| 5,462,949 | 10/1995 | Jones et al. | 514/324 |
| 5,462,950 | 10/1995 | Fontana | 514/324 |
| 5,468,746 | 11/1995 | Casagrande et al. | 514/235 |
| 5,480,888 | 1/1996 | Kodama et al. | 514/320 |
| 5,480,904 | 1/1996 | Bryant et al. | 514/443 |
| 5,482,949 | 1/1996 | Black et al. | 514/324 |
| 5,482,950 | 1/1996 | Bryant et al. | 514/324 |
| 5,491,173 | 2/1996 | Toivola et al. | 514/648 |
| 5,492,926 | 2/1996 | Cullinan et al. | 514/422 |
| 5,492,927 | 2/1996 | Glitter et al. | 514/443 |

FOREIGN PATENT DOCUMENTS

| | | |
|---|---|---|
| 85/00107 | 1/1985 | WIPO . |
| WO 85/00107 | 1/1985 | WIPO . |
| WO 90/01969 | 3/1990 | WIPO . |
| WO 91/15219 | 10/1991 | WIPO . |
| WO 91/15222 | 10/1991 | WIPO . |
| 92/06068 | 4/1992 | WIPO . |
| WO 92/08480 | 5/1992 | WIPO . |
| WO 92/18546 | 10/1992 | WIPO . |
| 92/19612 | 11/1992 | WIPO . |
| WO 92/19273 | 11/1992 | WIPO . |
| WO 92/21363 | 12/1992 | WIPO . |
| WO 93/07748 | 4/1993 | WIPO . |
| 93/09228 | 5/1993 | WIPO . |
| 93/09790 | 5/1993 | WIPO . |
| 93/10808 | 6/1993 | WIPO . |
| 93/11757 | 6/1993 | WIPO . |
| 93/19746 | 10/1993 | WIPO . |
| 94/04164 | 3/1994 | WIPO . |
| 94/09764 | 5/1994 | WIPO . |
| WO 94/09812 | 5/1994 | WIPO . |
| WO 94/10187 | 5/1994 | WIPO . |

OTHER PUBLICATIONS

K. Ohmi, et al., "Effect of K252a, A Protein Kinase Inhibitor, on the Proliferation of Vascular Smooth Muscle Cells", *Biochem. Biophys. Res. Comm.*, 173, 976–981 (1990).

G. K. Owens, et al., "Transforming Growth Factor–B–induced Growth Inhibition and Cellular Hypertrophy in Cultured Vascular Smooth Muscle Cells", *The Journal of Cell Biology*, 107, 771–780 (Aug., 1988).

C. F. Reilly, "Rat Vascular Smooth Muscle Cells Immortalized with SV40 Large T Antigen Possess Defined Smooth Muscle Cell Characteristics Including Growth Inhibition by Heparin", *J. Cell. Physiol.*, 142, 342–351 (1990).

P. L. Weissberg, et al., "Is Vascular Smooth Muscle Cell Proliferation Beneficial?", *Lancet*, 347, 305–307 (1996).

N. Koyama, et al., "Regulation of Smooth Muscle Cells Migration by a New Autocrine Migration Factor and TGF–beta", *Ciculation*, 84, Abstract No. 1829, II–459 (1991).

Z. Reiner, et al., "Antiestogen Tamoxifen Reduces Lipoprotein(a)", Abstracts, The Second International Conference on Lipoprotein (a), New Orleans, LA, p. 124 (Nov. 12–14, 1992).

A. Marzocchi, et al., translation of: "*Restenosis after Coronary Angioplasty: Its Pathogenesis and Prevention*", *Cardiologia*, 36, 309–320 (Dec. 1991).

D. J. Grainger, et al., "Active TGF–B is Depressed Five–Fold in Triple Vessel Disease Patients Compared with Syndrome X Patients", *J. Cell Biochem*, 18A, 267, Abstract no. E111 (1994).

D. J. Grainger, et al., "Mitogens for Adult Rat Aortic Vascular Smooth Muscle Cells in Serum–Free Primary Culture", *Cardiovascular Res.*, 28, 1238–1242 (1994).

J. Hofmann, et al., "Enhancement of the Antioproliferative Effect of cis–Diamminedichloroplatinum (II) and Nitrogen Mustard by Inhibitors of Protein Kinase C", *Int. J. Cancer*, 42, 382–388 (1988).

D. L. Hwang, et al., "Effects of Platelet–Contained Growth Factors (PDGF, EGF, IGF–1, and TGF–B) on DNA Synthesis in Porcine Aortic Smooth Muscle Cells in Culture", *Exp. Cell Res.*, 200, 358–360 (1992).

V. C. Jordan, "Long–Term Tamoxifen Therapy to Control or to Prevent Breast Cancer: Laboratory Concept to Clinical Trials", In: *Hormones Cell Biology and Cancer: Perspective and Potentials*, Alan R. Liss, Inc.; pp. 105–123 (1988).

C. Knabbe, et al., "Induction of Transforming Growth Factor–B by the Antiestrogens Droloxifene, Tamoxifen, and Toremifene in MCF-7 Cells", *Am. J. Clin. Oncol.*, 14, S15–S20, (1991).

N. Koyama, et al., "Regulation of Smooth Muscle Cells Migration by a New Autocrine Migration Factor and TGF–beta", *Abstracts from the 64th Scientific Sessions*, II–459 (1990).

J. R. Perez, et al., "Regulation of Adhesion and Growth of Fibrosarcoma Cells by NF–kb RelA Involves Transforming Growth Factor Beta", *Molecular and Cellular Biology*, 14, 5326–5332, (Aug. 1994).

Z. Reiner, et al., "Antiestogen Tamoxifen Reduces Lipoprotein (a)".

J. Schneiderman, et al., "Increased Type 1 Plasminogen Activator Inhibitor Gene Expression in Atherosclerotic Human Arteries", *Proc. Natl. Acad. Sci. USA*, 89, 6998–7002 (Aug. 1992).

B. Schoenemanne, et al., "The Differential Diagnoses of Spontaneous Pneumothorax and Pulmonary Lymphangioleimyomatosis Clinical Picture Diagnoses and Theory", *Chirag*, 61, 301–303 (1990), English Abstract only, reported in *Biosis*, 90, 432367 (1990).

R. S. Schwartz, et al., "The Restenosis Pardigm Revisted: An Alternative Proposal for Cellular Mechanisms", *JACC*, 20, 1284–1293 (Nov., 1992).

S. Sedlacek, "Estrogenic Properties of Tamoxifen on Serum Lipids in Postmenopausal Women with Breast Cancer (BCA)", *Breast Cancer Research and Treatment*, 14, Abstract No. 82, p. 153, (1989).

D. A. Shewmon, et al., "Tamoxifen and Estrogen Lower Circulating Lipoprotein(a) Concentrations in Healthy Postmenopausal Women", *Arteriosclerosis and Thrombosis*, 14, 1589–1593, (Oct. 1992).

D. A. Shewmon, et al., "Tamoxifen Decreases Lipoprotein (a) in Patients with Breast Cancer.", *Metabolism*, 43, 531–532 (May, 1994).

U. Siebenlist, et al., "Structure, Regulation and Function of NF–kB", *Annu. Rev. Cell. Biol.*, 10, 405–455, (1994).

P. Sismondi, et al., "Metaboic Effects of Tamoxifen in Postmenopause", *Anticancer Res.*, 14, 2237–2244 (1994).

A. D. Snow, et al., "Heparin Modulates the Composition of the Extracellular Matrix Domain Surrounding Arterial Smooth Muscle Cells", *Am. J. Path.*, 137, 313–330 (1990).

A. Stouffer, et al., "TGFbeta Has a Biphasic, Concentration Dependent Effect on EGF and PDGF–BB Induced Smooth Muscle Cell Proliferation", Session on Inflammation, Growth Regulatory Molecules & Atherosclerosis, *J. Cellular Biochem.*, Supplement 18A, Abstract No. A321, p. 288 (1994).

R. L. Wilensky, et al., "Direct Intraarterial Wall Injection of Microparticles Via a Catheter: A Potential Drug Delivery Strategy Following Angioplasty.", *Am. Heart J.*, 122, 1135–1140 (Oct. 1991).

N. N. Yang, et al., "Estrogen Receptor: One Transcription Factor, Two Genomic Pathways", *Calcified Tissue Intl.*, 54, 342, (1994).

Anderson et al., "Effects of Acetate Dialysate on Transforming Growth Factor $\beta_1$–interleukin and $\beta_2$–microglobulin Plasma Levels," *Kidney International*, 40, 1110–1117 (Oct. 1991).

Assoian et al., "Type $\beta$ Transforming Growth Factor in Human Platelets: Release During Platelet Degranulation and Action on Vascular Smooth Muscle Cells," *J. Cell. Biol.*, 102, 1217–1223 (Apr. 1986).

Attwood et al., "A Light Scattering Study on Oil–in–Water Microemulsions", *Int'l J. Pharm.*, 52, 165–171 (1989).

Bagdade et al., "Effects of Tamoxifen Treatment on Plasma Lipids and Lipoprotein Lipid Composition," *J. Clinical Endocrinology and Metabolism*, 70, 1132–1135 (1990).

Benita et al., "Submicron Emulsions as Colloidal Drug Carriers for Intravenous Administration: Comprehensive Physiochemical Characterization," *J. of Pharmaceutical Sciences*, 82 1069–1079 (Nov. 1993).

Bertelli et al., "Adjuvant Tamoxifen in Primary Breast Cancer: Influence on Plasma Lipids and Antithrombin III Levels," *Breast Cancer Res. and Treatment*, 12, 307–310 (1988).

Bier et al., "Arterial Remodeling: Importance in Primary Versus Restenoic Lesions," *JACC*, p. 139A, Abstract No. 875–96 (1994).

Bluming, "Hormone Replacement Therapy: Benefits and Risks for the General Postmenopausal Female Population and for Women with a History of Previously Treated Breast Cancer," *Seminars in Oncology*, 20, 662–674 (Dec. 1993).

Brott et al., "Vessel Remodeling After Angioplasty: Comparative Anatomic Studies," *JACC*, p. 138A, Abstract No. 875–43 (1994).

Bruengger et al., "Smooth Muscle Cell of the Canine Prostate in Spontaneous Benign Hyperplasia, Steroid Induced Hyperplasia and Estrogen or Tamoxifen Treated Dogs," *J. Urology*, 1208–1210 (Dec. 1983).

Bruning et al., "Tamoxifen, Serum Lipoproteins and Cardiovascular Risk," *Br. J. Cancer*, 58, 497–499 (1988).

Chander et al., "Pyrrolidino–4–iodotamoxifen and 4–iodotamoxifen, New Analogues of the Antiestrogen Tamoxifen for the Treatment of Breast Cancer," *Cancer Res.*, 51, 5851–5858 (Nov. 1, 1991).

Chao et al., Altered Cytokine Release in Peripheral Blood Mononuclear Cell Cultures from Patients with the Chronic Fatigue Syndrome, *Cytokine*, 3, 292–298 (Jul. 1991).

Charlier et al., "Tamoxifen in the Treatment of Breast Cancer," *J. Gynecol. Obstet. Biol. Reprod.* (Paris), 23, 751–756 (1994).

Clowes et al., "Kinetics of Cellular Proliferation after Arterial Injury–I. Smooth Muscle Growth in the Absence of Endothelium", *Laboratory Investigation*, 49, 327–333 (1983).

Clowes et al., "Kinetics of Cellular Proliferation after Arterial Injury–III. Endothelium and Smooth Muscle Growth in Chronically Denuded Vessels", *Laboratory Investigation*, 54, 295–303 (1986).

Clowes et al., "Mechanisms of Stenosis after Arterial Injury", *Laboratory Investigation*, 49, 208–215 (1983).

Clowes et al., "Significance of Quiescent Smooth Muscle Migration in the Injured Rat Carotid Artery", *Cir. Res.*, 56, 139–145 (Jan. 1985).

Cotton, "Restenosis Trials Suggest Role for Remodeling, Medical News and Perspective," *JAMA*, 271, 1302–1305 (1994).

Crissman et al., "Transformed Mammalian Cells are Deficient in Kinase–Mediated Control of Progression Through the G1 Phase of the Cell Cycle," *PNAS USA*, 88, 7580–7584 (Sep. 1991).

Danielpour et al., "Evidence for Differential Regulation of TGF–$\beta_1$ and TGF–$\beta_2$ Expression in Vivo by Sandwich Enzyme–linked Immunosorbent Assays," *Annals N.Y. Acad. Sci.*, 593, 300–302 (1990).

Danielpour et al., "Immunodetection and Quantitation of the Two Forms of Transforming Growth Factor–Beta (TGF–$\beta$1 and TGF–$\beta$2) Secreted by Cells in Culture," *J. Cell Physiol.*, 138, 79–86 (1989).

Danielpour, "Improved Sandwich Enzyme–linked Immunosorbent Assays for Transforming Growth Factor $\beta_1$," *J. Immunol. Methods*, 158, 17–25 (1993).

Dasch et al., Capture Immunoassays Specific for TGF–$\beta$1 and TGF–$\beta$2: Use in Pharmacokinetic Studies, *Annals N.Y. Acad. Sci.*, 593, 303–305 (1990).

DiMario et al., "Is the Mechanism of Restenosis Device–Independent? Serial Assessment with Intracoronary Ultrasound," *Circulation*, 90, p. I-24, Abstract No. 115 (1994).

Dimond et al., "TGF–Beta Shows Potential as Therapeutic Agent for Macular Holes," *Genetic Eng. News*, 7, 19 (Feb. 1, 1993).

Ebner et al., "Cloning of a Type I TGF–$\beta$ Receptor and Its Effect on TGF–$\beta$ Binding to the Type II Receptor", *Science*, 260, 1344–1348 (May 28, 1993).

Ellis et al., "In–Hospital Cost of Percutaneous Coronary Revascularization: Critical Determinants and Implications," *Circulation*, 92, 741–747 (1995).

Fanelli et al., "Restenosis Following Coronary Angioplasty", *Amer. Heart J.*, 119, 357–368 (Feb. 1990).

Farhat et al., "In Vitro Effect on Oestradiol on Thymidine Uptake in Pulmonary Vascular Smooth Muscle Cell: Role of the Endothelium," *Br. J. Pharamcol.*, 107, 679–683 (1992).

Faxon et al., "Restenosis Following Transluminal Angioplasty in Experimental Atherosclerosis", *Arteriosclerosis*, 4, 189–195 (May/Jun. 1984).

Fischer et al., "A Possible Mechanism in Arterial Wall for Mediation of Sex Difference in Atherosclerosis, Experimental and Molecular Pathology," 43, 288–296 (1985).

Friberg et al., "Microemulsions and Solubilization by Nonionic Surfactants," *Prog. Colloid and Polymer Sci.*, 56, 16–20 (1975).

Gasco et al., "In Vitro Permeation of Azelaic Acid from Viscosized Microemulsions", *International Journal of Pharmaceutics*, 69, 193–196 (1991).

Gasco et al, "Long–Acting Delivery Systems for Peptides: Reduced Plasma Testosterone Levels in Male Rats After a Single Injection," *Int. J. Pharmaceutics*, 62, 119–123 (1990).

Giachelli et al., "Osteopontin is Elevated during Neointima Formation in Rat Arteries and is a Novel Component of Human Atherosclerosis Plaques," *J. Clin. Invest.*, 92, 1686–1696 (Oct. 1993).

Gibbons et al., "The Emerging Concept of Vascular Remodeling," *New Engl. J. of Medicine*, 330, 1431–1438 (1994).

Glagov et al., "Compensatory Enlargement of Human Atherosclerotic Coronary Arteries", *New Engl. J. Med.*, 316, 1371–1375 (May 28, 1987).

Kakuta et al., "The Impact of Arterial Remodeling on the Chronic Lumen Size After Angioplasty in the Atherosclerotic Rabbit," *JACC*, p. 138A, Abstract No. 875–95 (1994).

Kakuta et al., "Differences in Compensatory Vessel Enlargement, Not Intimal Formation, Account for Restenosis After Angioplasty in the Hypercholesterolemic Rabbit Model," *Circulation*, 89, 2809–2815 (1994).

Kemp et al., "Inhibition of PDGF BB stimulated DNA synthesis in rat aortic vascular smooth muscle cells by the expression of a truncated PDGF receptor," *FEBS Letters*, 336 119–123 (Dec. 1993).

Knabbe et al., "Evidence that Transforming Growth Factor–$\beta$is a Hormonally Regulated Negative Growth Factor in Human Breast Cancer Cells," *Cell*, 48, 417–428 (Feb. 1987).

Koff et al., "Negative Regulation of G1 in Mammalian Cells: Inhibition of Cyclin E–Dependent Kinase by TGF–$\beta$," *Science*, 260, 536–538 (Apr. 23, 1993).

Kovach et al., "Serial Intravascular Ultrasound Studies Indicate that Chronic Recoil is an Important Mechanism of Restenosis Following Transcatheter Therapy," *JACC*, 21, p. 484A, Abstract No. 835–3 (1993).

Kuntz et al., "Defining Coronary Restenosis Newer Clinical and Angiographic Paradigms," *Circulation*, 88, 1310–1323 (Sep. 1993).

LaFont et al., "Post–Angioplasty Restenosis in the Atherosclerotic Rabbit: Proliferative Response or Chronic Constriction?," *Circulation*, 88, p. I–521, Abstract No. 2806 (1993).

Lehmann–Bruinsma et al., "Transforming Growth Factor–$\beta_2$ Suppression of Smooth Muscle Cell (SMC) Proliferation After Balloon Angioplasty of Rat Carotid Arteries," Abstract presented at the WSCI/WSAFCR Combined Plenary Session. *Clinical Res.*, 42, p. 4A (Feb 9–12, 1994).

Levy et al., "Drug Release from Submicronized o/w Emulsion: A New in Vitro Kinetic Evaluation Model", *International J. Pharmaceutics*, 66, 29–37 (1900).

Li et al., "Structure and Dynamics of Microemulsions which Mimic the Lipid Phase of Low–Density Lipoproteins", *Biochimica et Biophysica Acta*, 1042, 42–50 (1990).

Liaw et al., "Osteopontin Promotes Vascular Cell Adhesion and Spreading and is Chemotactic for Smooth Muscle Cells In Vitro," *Cir. Res.*, 74, 214–224 (Feb. 1994).

Lin et al., "Expression Cloning of the TGF–$\beta$ Type II Receptor, a Functional Transmembrane Serine/Threonine Kinase," *Cell*, 68, 775–785 (Feb. 21, 1992).

Linn et al., "Microemulsion for Intradermal Delivery of Cetyl Alcohol and Octyl Dimethyl Paba", *Drug Development and Industrial Pharmacy*, 16, 899–920 (1990).

Love et al., "Effects of Tamoxifen on Cardiovascular Risk Factors in Postmenopausal Women," *Annals of Internal Medicine*, 115, 860–864 (Dec. 1, 1991).

Love et al., "Effects of Tamoxifen Therapy on Lipid and Lipoprotein Levels in Postmenopausal Patients with Node–Negative Breast Cancer," *J. Natl. Cancer Inst.*, 82, 1327–1332 (Aug. 15, 1990).

Luo et al., "Chronic Vessel Constriction is an Imortant Mechanism of Restenosis After Balloon Angioplasty: An Intravascular Ultrasound Analysis,"*Circulation*, 90, p. I–61, Abstract No. 318 (1994).

Macander et al., "Balloon Angioplasty for Treatment of In–Stent Restenosis: Feasibility, Safety, and Efficacy," *Catheterization and Cardiovascular Diagnosis,* 32, 125–131 (1994).

Magarian et al., "The Medicinal Chemistry of Nonsteroidal Antiestrogens: A Review," *Current Medicinal Chemistry,* 1, 61–104 (1994).

Malcolmson et al., "A Comparison Between Nonionic Micelles and Microemulsions as a Means of Incorporating the Poorly Water Soluble Drug Diazepam", Abstract presented at the British Pharmaceutical Conference. *J. Pharm. Pharmacol.,* 42, 6P (Sep. 10–13, 1990).

Massague, "The Transforming Growth Factor–β Family", *Ann. Rev. Cell Biol.,* 6, 597–641 (1990).

McCaffrey et al., "Transforming Growth Factor–β Activity is Potentiated by Heparin via Dissociation of the Transforming Growth Factor–β/$\alpha_2$–Macroglobulin Inactive Complex," *J. Cell Biol.,* 109, 441–448 (Jul. 1989).

McCague et al., "An Efficient, Large–Scale Synthesis of Idoxifene {(E)–1–[4–{2–(N–pyrrolidino)ethoxy}phenyl]–1–(4–iodophenyl)–2–phenyl–1–butene}," *Organic Preparations and Procedures Int.,* 26, 343–346 (1994).

McCague et al., "Synthesis of 4–Stannylated Tamoxifene Analogues: Useful Precursors to Radiolabelled Idoxifene and Aziridinyl 4–Iodotamoxifene," *J. of Labelled Compounds and Radiopharmaceuticals,* 34, 297–302 (1993).

McCaroll et al., "Preliminary Studies on the Regulation of Secretion of Latent Transforming Growth Factor–β(TGF–β) by Endothelial Cells in Culture," *Clin. Chem.,* 36, p. 1152, Abstract No. 0934 (1990).

McCormick et al., "Retinoid–Tamoxifen Interaction in Mammary Cancer Chemoprevention," *Carcinogenesis,* 7, 193–196 (1986).

McDonald et al., "Fatal Myocardial Infarction in the Scottish Adjuvant Tamoxifen Trial,"*B. Med. J.,* 303, 435–437 (Aug. 24, 1991).

McLean et al., "cDNA sequence of human apolipoprotein (a) is homologous to plasminogen," *Nature,* 330, 132–137 (1987).

Merrilees et al., "Synthesis of TGF–$\beta_1$ by Vascular Endothelial Cells is Correlated with Cell Spreading," *J. Vasc. Res.,* 29, 376–384 (1992).

Mintz et al., "Chronic Compensatory Arterial Dilation Following Coronary Angioplasty: An Intravascular Ultrasound Study," *JACC,* p. 139A, Abstract No. 875–97 (1994).

Mintz et al., "Geometric Remodeling is the Predominant Mechanism of Clinical Restenosis After Coronary Angioplasty," *JACC,* p. 138A, Abstract 875–42 (1994).

Mintz et al., "Mechanisms of Later Arterial Responses to Transcatheter Therapy: A Serial quantitative Angiographic and INtravascular Ultrasound Study," *Circulation,* 90, p. I–24, Abstract No. 117 (1994).

Morisaki et al., "Effects of Transforming Growth Factor–$\beta_1$ on Growth of Aortic Smooth Muscle Cells: Influences of Interaction with Growth Factors, Cell State, Cell Phenotype, and Cell Cycle," *Atherosclerosis,* 88, 227–234 (1991).

Nakagawa et al., "A Case of Acute Myocardial Infarction Intracoronary thrombosis in Two Major Arteries Due to Hormone Therapy," *Angiology,* 45, 333–338 (May 1994).

Nunes et al., "Viramins C and E Improve the Response to Coronary Balloon Injury in the Pig: Effect of Vascular Remodeling," *Circulation,* 88, p. I–372, Abstract No. 1994 (Oct. 1993).

O'Brien et al., "Osteopontin mRNA and Protein are Overexpressed in Human Coronary Atherectomy Specimens: Clues to Lesion Calcification," *Circulation,* 88, p. I–619, Abstract No. 3330 (1993).

O'Connor–McCourt et al., "Latent Transforming Growth Factor–β in Serum: A Specific Complex with $\alpha_2$–macroglobulin," *J. Biol. Chem.,* 262, 14090–14099 (Oct. 15, 1987).

Osborne et al., "Microemulsions as Topical Drug Delivery Vehicles: In Vitro Trandermal Studies of a Model Hydrophilic Drug", *J. Pharm. Pharmacol.,* 43, 451–454 (1991).

Osipow, "Transparent Emulsion," *J. of the Soc. of Cosmetic Chemists,* 277–285.

Ozer et al., "New Role of Low Density Lipoproteins and Vitamin E in the Pathogenesis of Athersclerosis," *Bioch. Mol. Biol. Int.,* 35, 117–124 (Jan. 1995).

Pathak et al., "Enhanced Stability of Physostigmine Salicylate in Submicron o/w Emulsion", *International J. of Pharmaceutics,* 65, 169–175 (1990).

Podzimek et al., "O/W Microemulsions", *J. Dispersion Science and Technology,* 1, 341–359 (1980).

Popma et al., "Factors Influencing Restenosis after Coronary Angioplasty," *Am. J. of Med.,* 88, 1–16N–1–24N (Jan. 1990).

Post et al., "Restenosis is Partly Due to Intimal Hyperplasia and Partly to Remodeling of the Injured Arterial Wall," *Eur. Heart J.,* 14, p. 201, Abstract No. P1164 (1993).

Post et al., "Which Part of the Angiographic Diameter Reduction After Balloon Dilation is Due to Intimal Hyperplasia?," *JACC,* 21, p. 36A, Abstract No. 851–95 (Feb. 1993).

Potter et al., "A Mechanistic Hypothesis for DNA Adduct Formation Following Hepatic Oxidative Metabolism," *Carcinogenesis,* 15, 439–442 (1994).

Pouton, "Self–Emulsifying Drug Delivery Systems: Assessment of the Efficiency of Emulsification," *Int. J. of Pharmaceutics,* 27, 335–348 (1985).

Reid et al., "Fragmentation of DNA in P388$D_1$ Macrophages Exposed to Oxidized Low–Density Lipoprotein," *FEBS Letters,* 332, 218–220 (Aug. 1992).

Ross et al., "Chronic Inflammation, PDGF, TGF, and Smooth Muscle Proliferation," *Molecular Mechanisms of Vascular Diseases,* p. 96, Abstract No. G006 (1991).

Sagitani et al., "Microemulsion Systems with a Nonionic Cosurfactant", *J. Dispersion Science and Technology,* 1 (2), 151–164 (1980).

Sanders et al., "Controlled Release of a Luteinizing Hormone–Releasing Hormone Analogue from Poly(d,l–lactide–co–glycolide) Microspheres", *J. Pharmaceutical Science,* 73, 1294–1297 (Sep. 1984).

Schlingemann et al., "Expression of the High Molecular Weight Molenoma–Associated Antigen by Pericytes During Angiogenesis in Tumors and in Healing Wounds", *Amer. J. Pathology,* 136, 1393–1405 (Jun. 1990).

Schneiderman et al., "Increased Type 1 Plasminogen Activator Inhibitor Gene Expression in Atherosclerotic Human Arteries", *PNAS (USA),* 89, 6998–7002 (Aug. 1992).

Schwartz et al., "The Restenosis Paradigm Revisited: An Alternative Proposal for Cellular Mechanisms," *JACC,* 20, 1284–1293 (Nov. 1, 1992).

Schwartz et al., "Maintenance of Integrity in Aortic Endothelium," *Fed. Proc.,* 39, 2618–2625 (Jul. 1980).

Shanahan et al., "Isolation of Gene Markers of Differentiated and Proliferating Vascular Smooth Muscle Cells," *Cir. Res.,* 73, 193–204 (1993).

Shewmon et al., "Tamoxifen Lowers Lp(a) in Males with Heart Disease," *Supplement I Cir.*, 86, I–388, Abstract No. 1345 (Oct. 1992).

Shoji et al., "Enhancement of Anti–Inflammatory Effects of Biphenylylacetic Acid by its Incorporation into Lipid Microspheres", *J. Pharm. Pharmacol.*, 38, 118, 118–121 (1986).

Singh et al., "Phylogenetic Analysis of Platelet–derived Growth Factor by Radio–Receptor Assay," *J. Cell Biol.*, 95, 667–671 (Nov. 1982).

Snow et al., "Heparin Modulates the Composition of the Extracellular Matrix Surrounding the Arterial Smooth Muscle Cells," *J. Path.*, 137, 313–330 (1990).

Streuli et al., "Extracellular Matrix Regulates Expression of the TGF–$\beta_1$ Gene,"*J. of Cell Biol.*, 120, 253–260 (Jan. 1993).

Suckling, "Emerging Strategies for the Treatment of Atherosclerosis as Seen from the Patent Literature," *Biochem. Soc. Trans.*, 21, 660–662 (Mar. 30, 1993).

Tanaka et al., "Prominent Inhibitory Effects of Transilast on Migration and Proliferation of a Collagen Synthesis by Vascular Smooth Muscle Cells," *Atherosclerosis*, 107, 179–185 (1994).

Topol, "The Restenosis 'Antitheory'," *Mayo Clin. Proc.*, 68, 88–90 (Jan. 1993).

Vanhoutte, "Hypercholesterolaemia, Atherosclerosis and Release of Endothelium–Derived Relaxing Factor by Aggregating Platelets," *Eur. Heart J.* 12, Supp. E, 25–32 (1991).

Vargas et al., "Oestradiol Inhibits Smooth Muscle Cell Proliferation of Pig Coronary Artery," *Br. J. Pharmacol.*, 109, 612–617 (1993).

Wakefield et al., "Latent Transforming Growth Factor–$\beta$ from Human Platelets: A High Molecular Weight Complex Containing Precursor Sequences," *J. Biol. Chem.*, 263, 7646–7654 (Jun. 5, 1988).

Wakefield et al., "Recombinant Latent Transforming Growth Factor–$\beta_1$ has a Longer Plasma Half–Life in Rats than Active Transforming Growth Factor–$\beta_1$, and a Different Tissue Distribution," *J. Clin. Invest.*, 86, 1976–1984 (Dec. 1990).

Watson et al., "TGF–$\beta_1$ and 25–Hydroxycholesterol Stimulate Osteoblast–Like VAscular Cells to Calcify," *J. Clin. Invest.*, 93, 2106–2113 (May 1994).

Weissberg et al., "The Endothelin Peptides ET–1, ET–2, ET–3 and Sarafotoxin S6b are Ecomitogenic with Platelet–Derived Growth Factor for Vascular Smooth Muscle Cells," *Atherosclerosis*, 85, 257–262 (1990).

Wolf et al., "Antibodies Against Transforming Growth Factor–$\beta_1$ Suppress Intimal Hyperplasia in a Rat Model," *J. Clin. Invest.*, 93, 1172–1178 (Mar. 1994).

Zuckerman et al., "Cytokine Regulation of Macrophage apo E Secretion: Opposing Effects of GM–CSF and TGF–$\beta$," *Atherosclerosis*, 96, 203–214 (1992).

Zuckerman et al., "Exogenous glucocorticoids Increase Macrophage Secretion of E by Cholesterol–Independent Pathways," *Atherosclerosis*, 103, 43–54 (1993).

Wolinsky et al., "Use of a perforated balloon catheter to deliver concentrated heparin into the wall of the normal canine artery," *J. Am. Coll. Cardiol.*, vol. 15, No. 2, Feb. 1990, pp. 475–481.

Forrester et al., "A paradigm for restenosis based on cell biology: clues for the development of new preventive therapies," *J. Am. Coll. Cardiol.*, vol. 17, No. 3, Mar. 1991, pp. 758–769.

Barath et al., "Low dose of antitumor agents prevents smooth muscle cell proliferation after endothelial injury," *J. Am. Coll. Cardiol.*, vol. 13, No. 2, Feb. 1989, p. 252A.

International Search Report issued in PCT/US94/05265. (1994).

Butta et al., "Induction of transforming growth factor B1 in human breast cancer in vivo following tamoxifen treatment", *Cancer Research*, vol. 52, pp. 4261–4264, Aug. 1, 1992.

Grainger et al., "Hexamethylenebisacetamide selectively inhibits the pro–liferation of human and rat vascular smooth–muscle cells", *Biochem. J.*, vol. 283, pp. 403–408. (1992).

Grainger et al., "A large accumulation of non–muscle myosin occurs at first entry into M phase in rat vascular smooth muscle cells," *Biochem. J.*, vol. 277, pp. 145–151, (1991).

Grainger et al., "Transforming growth factor B decreases the rate of pro–liferation of rat vascular smooth muscle cells by extending the $G_2$ phase of the cell cycle and delays the rise in cyclic AMP before entry into M phase," *Biochem. J.*, vol. 299, pp. 227–235, (1994).

Grainger et al., "Tamoxifen decreases the rate of proliferation of rat vascular smooth–muscle cells in culture by inducing production of transforming growth factor B", *Biochem. J.*, vol. 294, pp. 109–112 (1993).

Grainger et al., "Proliferation of human smooth muscle cells promoted by lipoprotein(a)", *Science*, vol. 260, Jun. 11, 1993, pp. 1655–1658.

Grainger et al., "Heparin decreases the rate of proliferation of rat vascular smooth muscle cells by releasing transforming growth factor B–like activity from serum", *Cardio. Res.*, vol. 27, pp. 2238–2247, (1993).

Hanke et al., "Inhibition of cellular proliferation after experimental balloon angioplasty by low molecular weight heparin", *Circulation*, vol. 85, No. 4, pp. 1548–1556, Apr. 1992.

Kemp et al., "The Id gene is activated by serum but is not required for de–differentiation in rat vascular smooth muscle cells", *Biochem. J.*, vol. 277, pp. 285–288, (1991).

Kirschenlohr et al., "Adult human aortic smooth muscle cells in culture produce active TGF–B", *Am. J. Physiol.*, vol. 265, pp. C571–C576, (1993).

Kreuzer et al., "Lipoprotein(a) displays increased accumulation compared to low density lipoprotein in the murine arterial wall", *Chem. and Phys. of Lipids*, vol. 67, pp. 175–190, (1994).

Lefer, Allan M., "Role of transforming growth factor B in cardioprotection of the ischaemic–reperfused myocardium", in *Growth Factors and the Cardiovascular System*, (P. Cummins, Ed.), Kluwer, London, (1993).

Lefer et al., "Mechanism of the cardioprotective effect of transforming growth factor B 1 in feline myocardial ischemia and reperfusion", *Proc. Natl. Acad. Sci.* USA, vol. 90, pp. 1018–1022, (Feb. 1993).

Lefer et al., "Mediation of cardioprotection to transforming growth factor B", *Science*, vol. 249, pp. 61–64, Jul. 6, 1990.

Lopez–Casillas et al., "Betaglycan presents ligand to the TGF–B signaling receptor", *Cell*, vol. 73, pp. 1435–1444, Jul. 2, 1993.

Lui, M.W. et al., "Restenosis after coronary angioplasty potential biologic determinants and role of intimal hyperplasia", *Circulation*, vol. 79, No. 6, pp. 1374–1387, Jun. 1989.

Metcalfe et al., "Protein markets of lesion development in the vessels of transgenic APO (a) mice", *J. of Cell. Biochem.*, vol. 18A, p. 280, (1994).

Nabel et al., "Direct transfer of transforming growth factor B1 gene into arteries stimulates fibrocellular hyperplasia", *Proc. of the Natl. Acad. of Sci.* USA, vol. 90, pp. 10759–10763, Nov. 1993.

Nikol et al., "Expression of transforming growth factor B1 is increased in human vascular restenosis lesions", *J. of Clin. Invest.*, vol. 90, pp. 1582–1592, (1992).

Rauterberg et al., "Collagens in atherosclerotic lesions", *Current Topics in Pathology*, vol. 87, pp. 163–192, (1993).

Ross, Russell, "The pathogenesis of atherosclerosis: a perspective for the 1990's", *Nature*, vol. 362, pp. 801–809, Apr. 29, 1993.

Schwartz, R.S. et al., "Restenosis after balloon angioplasty, a practical proliferative model in porcine coronary arteries", *Circulation*, vol. 82, No. 6, pp. 2190–2200, 1990.

Shewmon et al., "Tamoxifen lowers Lp(a) in males with heart disease", *Circulation*, vol. 86, p. I–338, Oct. 1992.

Steele et al., "Balloon angioplasty, natural history of the pathophysiological response to injury in a pig model", *Circulation Research*, vol. 57, No. 1, pp. 105–112, Jun. 1985.

Streuli et al., "Extracellular matrix regulates expression of the TGF–B1 gene", *J. of Cell Biol.*, vol. 120, No. 1, pp. 253–260, Jan. 1993.

Tice and Cowsar, "Biodegradable controlled–release parenteral systems", *Pharmaceutical Technology*, Nov. 1984, pp. 26–35.

Weissberg et al., "Effects of TGF–B on vascular smooth muscle cell growth", in *Growth Factors and the Cardiovascular System*, (Cummins, P. ed.), Kluwer Academic Publishers, pp. 189–205, (1993).

Weissberg et al., "Approaches to the development of selective inhibitors of vascular smooth muscle cell proliferation", *Cardio. Res.*, vol. 27, pp. 1191–1198, (1993).

Package Insert for Nolvadex®(1992).

PREVENTION AND TREATMENT OF PATHOLOGIES ASSOCIATED WITH ABNORMALLY PROLIFERATIVE SMOOTH MUSCLE CELLS

RELATED APPLICATIONS

This application is a continuation-in-part of U.S. Ser. No. 08/061,714, filed May 13, 1993, now abandoned.

FIELD OF THE INVENTION

This invention relates generally to the prevention and treatment of conditions characterized by abnormal smooth muscle cell proliferation. More specifically, mechanisms for in vivo vascular smooth muscle cell proliferation modulation and agents that impact those mechanisms are discussed.

BACKGROUND OF THE INVENTION

Many pathological conditions have been found to be associated with smooth muscle cell proliferation. Such conditions include restenosis, atherosclerosis, coronary heart disease, thrombosis, myocardial infarction, stroke, smooth muscle neoplasms such as leiomyoma and leiomyosarcoma of the bowel and uterus, uterine fibroid or fibroma, and obliterative disease of vascular grafts and transplanted organs. The mechanism of abnormal smooth muscle cell proliferation is not yet well understood.

For example, percutaneous transluminal coronary angioplasty (PTCA) is widely used as the primary treatment modality in many patients with coronary artery disease. PTCA can relieve myocardial ischemia in patients with coronary artery disease by reducing lumen obstruction and improving coronary flow. The use of this surgical procedure has grown rapidly, with 39,000 procedures performed in 1983, nearly 150,000 in 1987, 200,000 in 1988, 250,000 in 1989, and over 500,000 PTCAs per year are estimated by 1994. Stenosis following PTCA remains a significant problem, with from 25% to 35% of the patients developing restenosis within 1 to 3 months. Restenosis results in significant morbidity and mortality and frequently necessitates further interventions such as repeat angioplasty or coronary bypass surgery. No surgical intervention or post-surgical treatment (to date) has proven effective in preventing restenosis.

The processes responsible for stenosis after PTCA are not completely understood but may result from a complex interplay among several different biologic agents and pathways. Viewed in histological sections, restenotic lesions may have an overgrowth of smooth muscle cells in the intimal layers of the vessel. Several possible mechanisms for smooth muscle cell proliferation after PTCA have been suggested.

Compounds that reportedly suppress smooth muscle proliferation in vitro may have undesirable pharmacological side effects when used in vivo. Heparin is an example of one such compound, which reportedly inhibits smooth muscle cell proliferation in vitro but when used in vivo has the potential adverse side effect of inhibiting coagulation. Heparin peptides, while having reduced anti-coagulant activity, have the undesirable pharmacological property of a short pharmacological half-life. Attempts have been made to solve such problems by using a double balloon catheter, i.e., for regional delivery of the therapeutic agent at the angioplasty site (e.g., U.S. Pat. No. 4,824,436), and by using biodegradable materials impregnated with a drug, i.e., to compensate for problems of short half-life (e.g., U.S. Pat. No. 4,929,602).

At least five considerations would, at first blush, appear to preclude use of inhibitory drugs to prevent stenosis resulting from overgrowth of smooth muscle cells. First, inhibitory agents may have systemic toxicity that could create an unacceptable level of risk for patients with cardiovascular disease. Second, inhibitory agents might interfere with vascular wound healing following surgery and that could either delay healing or weaken the structure or elasticity of the newly healed vessel wall. Third, inhibitory agents that kill smooth muscle cells could damage surrounding endothelium and/or other medial smooth muscle cells. Dead and dying cells also release mitogenic agents that might stimulate additional smooth muscle cell proliferation and exacerbate stenosis. Fourth, delivery of therapeutically effective levels of an inhibitory agent may be problematic from several standpoints, such as the following: a) delivery of a large number of molecules into the intercellular spaces between smooth muscle cells may be necessary to establish favorable conditions for allowing a therapeutically effective dose of molecules to cross the cell membrane; b) delivery of an inhibitory drug into the intracellular compartment where its action is exerted may be difficult to control; and c) optimizing the association of the inhibitory drug with its intracellular target (e.g., a ribosome) while minimizing intercellular redistribution of the drug (e.g., to neighboring cells) may be difficult. Fifth, because smooth muscle cell proliferation takes place over several weeks it would appear a priori that the inhibitory drugs should also be administered over several weeks, perhaps continuously, to produce a beneficial effect.

As is apparent from the foregoing, many problems remain to be solved in the use of inhibitory drugs to effectively treat smooth muscle cell proliferation. It would be highly advantageous to develop new compositions or methods for inhibiting stenosis due to proliferation of vascular smooth muscle cells following, for example, traumatic injury to vessels rendered during vascular surgery.

SUMMARY OF THE INVENTION

TGF-beta activators and TGF-beta production stimulators may be employed in the practice of the present invention to prevent or treat conditions characterized by inappropriate proliferation of smooth muscle cells, such as the prevention or reduction of restenosis following angioplasty or other vascular trauma. Such TGF-beta activators and production stimulators inhibit abnormal proliferation of smooth muscle cells. A preferred TGF-beta activator/production stimulator is trans-2-[4-(1,2-diphenyl-1-butenyl)phenoxy]-N,N-dimethylethylamine as well as functional equivalents, analogs or derivatives thereof.

The amount of TGF-beta activator or production stimulator administered is selected to treat vascular trauma of differing severity, with smaller doses being sufficient to treat lesser vascular trauma such as in the prevention of vascular rejection following graft or transplant. TGF-beta activators or production stimulators that are not characterized by an undesirable systemic toxicity profile at a prophylactic dose are also amenable to chronic use for prophylactic purposes with respect to disease states involving proliferation of vascular smooth muscle cells over time (e.g., atherosclerosis, coronary heart disease, thrombosis, myocardial infarction, stroke, smooth muscle neoplasms such as leiomyoma and leiomyosarcoma of the bowel and uterus, uterine fibroid or fibroma and the like). For prevention of restenosis, a large dose is preferably administered before or during the traumatic procedure (e.g., angioplasty). After the traumatic procedure is conducted, a series of smaller doses is administered over time to maintain an anti-proliferative effect for a time sufficient to substantially reduce the risk of or to prevent restenosis. A preferred therapeutic protocol duration for this purpose is from about 3 to about 26 weeks.

Further provided is a method for upregulating cellular mRNA coding for TGF-beta. Cells (e.g., smooth muscle cells) amenable to such metabolic manipulation are identified in the manner described herein and are exposed to an effective amount of a TGF-beta mRNA regulator (i.e., a subset of TGF-beta production stimulators). In this manner, TGF-beta production is stimulated, thereby inhibiting the abnormal proliferation of smooth muscle cells.

In addition, methods for using TGF-beta to maintain and increase vessel lumen diameter in a diseased or injured mammalian vessel are described. Further, methods for preventing or reducing atherosclerosis in a mammal are provided. Methods for determining TGF-beta in vitro are also presented.

DETAILED DESCRIPTION OF THE INVENTION

Figure 1:
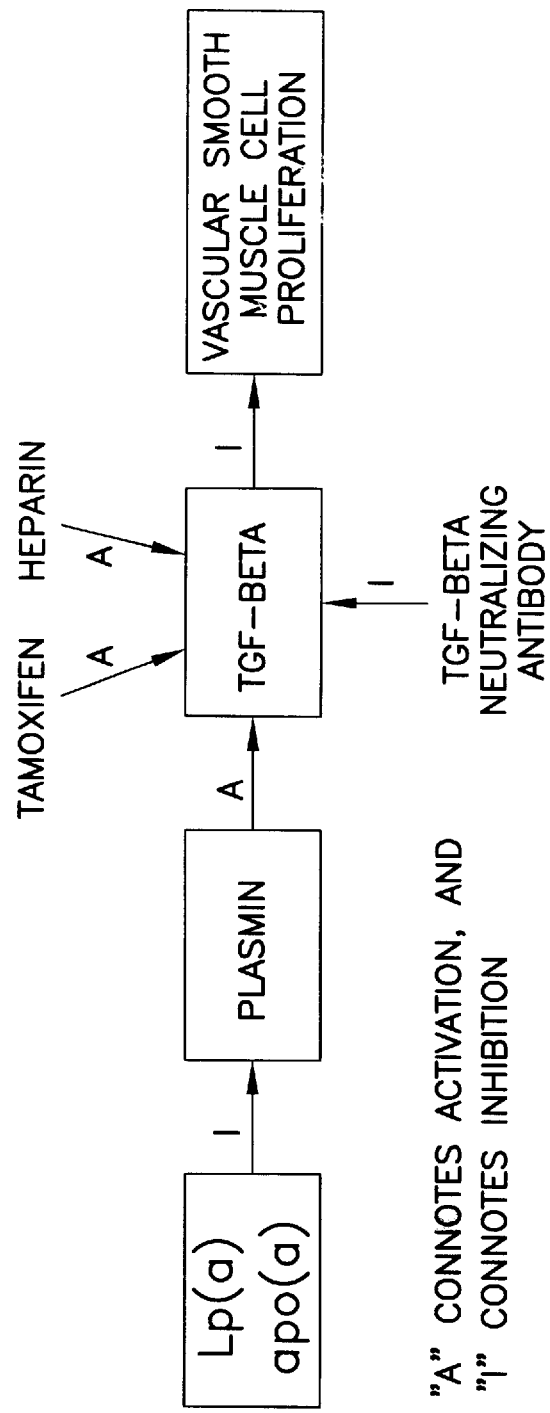
FIGS. 1 and 2 depict pathways for the modulation of vascular smooth muscle cell proliferation in vivo.

As used herein the following terms have the meanings as set forth below:

"Proliferation," means an increase in cell number, i.e., by mitosis of the cells.

"Abnormal or Pathological or Inappropriate Proliferation" means division, growth or migration of cells occurring more rapidly or to a significantly greater extent than typically occurs in a normally functioning cell of the same type.

"Expressed" means mRNA transcription and translation with resultant synthesis, glycosylation, and/or secretion of a polypeptide by a cell, e.g., chondroitin sulfate proteoglycan (CSPG) synthesized by a vascular smooth muscle cell or pericyte.

"Tamoxifen" includes trans-2-[4-(1,2-diphenyl-1-butenyl)phenoxy]-N,N-dimethylethylamine which is capable of enhancing the production or activation of TGF-beta. The activated form of TGF-beta, in turn, inhibits vascular smooth muscle cell proliferation. Functional equivalents and derivatives of the aforementioned chemical compound are also included within the scope of the term "tamoxifen" for the purposes of this disclosure. Exemplary tamoxifen functional equivalents are plasmin, heparin, angiotensin II, hexamethylene bisacetamide (HMBA), compounds capable of reducing the level or inactivating the lipoprotein Lp(a) or the glycoprotein apolipoprotein(a) and derivatives or analogs thereof. Tamoxifen is used herein as a prototypical TGF-beta activator/production stimulator.

"TGF-beta" includes transforming growth factor-beta as well as functional equivalents, derivatives and analogs thereof. The TGF-beta isoforms are a family of multifunctional, disulfide-linked dimeric polypeptides that affect proliferation and differentiation of various cells types. TGF-beta is a polypeptide produced in a latent propeptide form having, at this time, no identified biological activity. To be rendered active and, therefore, capable of inhibiting vascular smooth muscle cell proliferation, the propeptide form of TGF-beta must be cleaved to yield active TGF-beta.

"TGF-beta activator" includes moieties capable of directly or indirectly activating the latent form of TGF-beta to the active form thereof. Plasmin, plasmin activators, tamoxifen as well as analogs, derivatives or functional equivalents thereof are exemplary TGF-beta activators useful in the practice of the present invention.

"TGF-beta production stimulator" includes moieties capable of directly or indirectly stimulating the production of TGF-beta (generally the latent form thereof). Such TGF-beta production stimulators may be TGF-beta mRNA regulators (i.e., moieties that increase the production of TGF-beta mRNA), enhancers of TGF-beta mRNA expression or the like.

"Direct" action implies that the TGF-beta activator acts on the latent form of TGF-beta. Such direct action, when applied to TGF-beta production stimulators, indicates that cells upon which the production stimulator acts increase TGF-beta mRNA production or expression of TGF-beta.

"Indirect" action implies that the TGF-beta activator acts on a moiety that itself or through one or more other moieties acts on latent TGF-beta. Such indirect action, when applied to TGF-beta production stimulators, indicates that the stimulators act on a moiety that itself or through one or more other moieties acts on a population of cells to stimulate the production of TGF-beta mRNA or the expression of TGF-beta.

For the purposes of this description, the prototypical cells, upon which the effects of TGF-beta activators or production stimulators are felt, are smooth muscle cells and pericytes derived from the medial layers of vessels and adventitia vessels which proliferate in intimal hyperplastic vascular sites following injury, such as that caused during PTCA. TGF-beta activators and production stimulators are not restricted in use for therapy following angioplasty; rather, the usefulness thereof will be proscribed by their ability to inhibit abnormal cellular proliferation, for example, of smooth muscle cells and pericytes in the vascular wall. Thus, other aspects of the invention include TGF-beta activators or production stimulators used in early therapeutic intervention for reducing, delaying, or eliminating (and even reversing) atherosclerotic plaques and areas of vascular wall hypertrophy and/or hyperplasia. TGF-beta activators and production stimulators also find utility for early intervention in pre-atherosclerotic conditions, e.g., they are useful in patients at a high risk of developing atherosclerosis or with signs of hypertension resulting from atherosclerotic changes in vessels or vessel stenosis due to hypertrophy of the vessel wall.

TGF-beta activators or production stimulators of the invention are useful for inhibiting the pathological proliferation of vascular smooth muscle cells, e.g., for reducing, delaying, or eliminating stenosis following angioplasty. As used herein the term "reducing" means decreasing the intimal thickening that results from stimulation of smooth muscle cell proliferation following angioplasty, either in an animal model or in man. "Delaying" means delaying the time until onset of visible intimal hyperplasia (e.g., observed histologically or by angiographic examination) following angioplasty and may also be accompanied by "reduced" restenosis. "Eliminating" restenosis following angioplasty means completely "reducing" intimal thickening and/or completely "delaying" intimal hyperplasia in a patient to an extent which makes it no longer necessary to surgically intervene, i.e., to re-establish a suitable blood flow through the vessel by repeat angioplasty, atheroectomy, or coronary artery bypass surgery. The effects of reducing, delaying, or eliminating stenosis may be determined by methods routine to those skilled in the art including, but not limited to, angiography, ultrasonic evaluation, fluoroscopic imaging, fiber optic endoscopic examination or biopsy and histology.

High levels of lipoprotein Lp(a) are known to constitute a major risk factor for atherosclerosis, coronary heart disease and stroke. One symptom associated with such conditions and other problems, such as restenosis following balloon angioplasty and other pathogenic conditions, is the proliferation or the migration of smooth muscle cells. No direct link between Lp(a) and proliferation of vascular smooth muscle cells had been established in the prior art.

An in vivo pathway for the modulation of vascular smooth muscle cell proliferation is shown in FIG. 1. This mechanism is believed to constitute a portion of the mechanism that maintains vascular smooth muscle cells in a non-proliferative state in healthy vessels.

Vascular smooth muscle cell proliferation is inhibited by an active form of TGF-beta. Tamoxifen has been shown by the experimentation detailed in Example 1 hereof to stimulate both the production and the activation of TGF-beta. Heparin stimulates the activation of TGF-beta by affecting the release of the active form of TGF-beta from inactive complexes present in serum. TGF-beta neutralizing antibodies inhibit the activity of TGF-beta, thereby facilitating the proliferation of vascular smooth muscle cells. The apparent in vivo physiological regulator of the activation of TGF-beta is plasmin. Plasmin is derived from plasminogen through activation by, for example, tPA (tissue plasminogen activator). Plasminogen and, therefore, plasmin activity is inhibited by the lipoprotein Lp(a) or apolipoprotein(a) (apo (a)), thereby decreasing the activation of the latent form of TGF-beta and facilitating proliferation of vascular smooth muscle cells.

Figure 2:
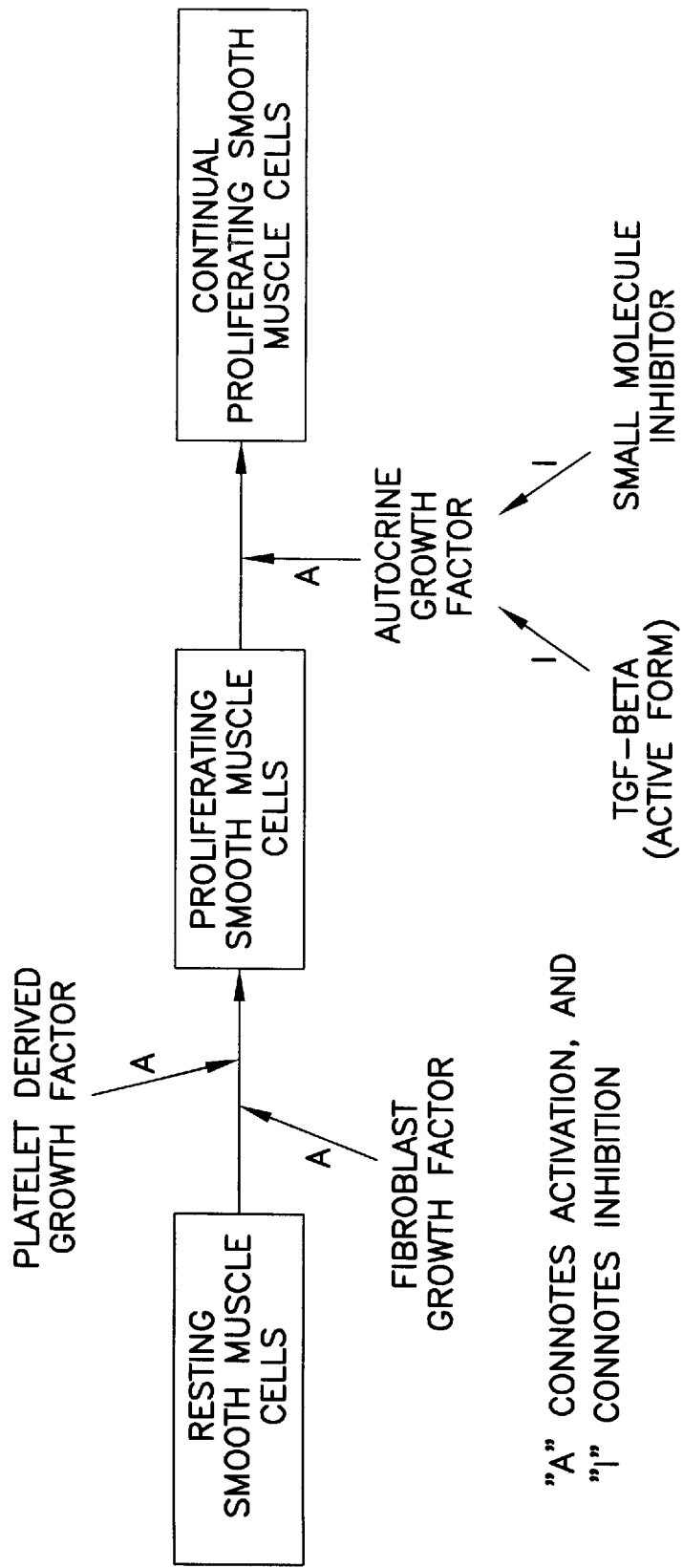

An additional pathway for the modulation of vascular smooth muscle cell proliferation is shown in FIG. 2. Resting smooth muscle cells constitute cells in their normal, quiescent non-proliferative state. Such resting smooth muscle cells may be converted to proliferating smooth muscle cells through activation by platelet derived growth factor (PDGF), fibroblast growth factor (FGF) or other stimulatory moieties. The proliferating smooth muscle cells may be converted to continual proliferating smooth muscle cells (i.e., smooth muscle cells capable of generating a pathological state resulting from over-proliferation thereof) by an autocrine growth factor. This growth factor is believed to be produced by proliferating smooth muscle cells. An increased level of autocrine growth factor, which can be inhibited by the active form of TGF-beta or an appropriately structured (i.e., designed) small molecule inhibitor, is believed to mediate the production of continual proliferating smooth muscle cells.

Lp(a) consists of low density lipoprotein (LDL) and apo(a). Apo(a) shares approximately 80% amino acid identity with plasminogen (see MacLean et al., *Nature*, 330: 132, 1987). Lp(a) has been found to inhibit cell-associated plasminogen activity (see, for example, Harpel et al., *Proc. Natl. Acad. Sci. USA*, 86: 3847, 1989). Experiments conducted on human aortic vascular smooth muscle cells derived from healthy transplant donor tissue, cultured in Dulbecco's modified Eagles medium (DMEM)+10% fetal calf serum (FCS) as described in Grainger et al., *Biochem. J.*, 283: 403, 1992, indicated the following:

1) Addition of Lp(a) to sub-confluent human vascular smooth muscle cells stimulated their proliferation in a dose dependent manner (addition of 500 nM Lp(a) to human vascular smooth muscle cells caused a reduction in doubling time from 82+/−4 hours to 47+/−4 hours);

2) Addition of apo(a) had a similar effect, although a higher concentration of apo(a) appeared to be required therefor;

3) Addition of LDL at varying concentrations up to 1 micromolar had no effect on proliferation.

One possible mode of action for Lp(a) and apo(a) is competitive inhibition of surface-associated plasminogen activation, which in turn inhibits the subsequent activation of TGF-beta by plasmin. TGF-beta is a potent growth inhibitor of a number of anchorage-dependent cells, including smooth muscle cells. TGF-beta is produced as a latent propeptide having a covalently linked homodimer structure in which the active moiety is non-covalently linked to the amino-terminal portion of the propeptide. Latent TGF-beta must be cleaved (e.g., in vitro by acid treatment or in vivo by the serine protease plasmin) in order to become capable of inhibiting the proliferation of vascular smooth muscle cells. Plasmin is therefore a leading candidate to be a physiological regulator of TGF-beta.

The hypothesis that Lp(a) and apo(a) were acting on cultured human vascular smooth muscle cells by interfering with activation of latent TGF-beta was tested. In support of this hypothesis, an observation was made that plasmin activity associated with vascular smooth muscle cells was reduced 7-fold by Lp(a) and 5-fold by apo(a). The plasmin activity in the conditioned medium was also reduced by Lp(a) and apo(a) by about 2-fold, but was much lower than cell-associated plasmin activity in vascular smooth muscle cell cultures. These observations are consistent with previous findings that Lp(a) is a more potent inhibitor of surface-associated, rather than fluid phase, plasminogen activation.

To exclude the possibility that Lp(a) was affecting the synthesis of plasminogen activators rather than plasminogen activation, plasminogen activator levels in human vascular smooth muscle cell cultures were measured in the presence and absence of the lipoproteins and in the presence of a large excess of plasminogen, so that the lipoproteins present would not significantly act as competitive inhibitors. Total plasminogen activator activity was not affected by the presence of any of the lipoproteins in the vascular smooth muscle cell cultures. For example, plasminogen activator activity in the conditioned medium remained at 0.7+/−0.6 mU/ml with Lp(a) additions up to 500 nM.

Lp(a) and apo(a) both reduced the level of active TGF-beta by more than 100-fold compared to control or LDL-treated cultures. The level of total latent plus active TGF-beta measured by ELISA as described in Example 1 was unaffected by the presence of Lp(a) or apo(a), however. These facts lead to the conclusion that Lp(a) stimulates proliferation of human vascular smooth muscle cells by inhibiting plasmin activation of latent TGF-beta to active TGF-beta.

To further test this conclusion and exclude the possibility that Lp(a) was acting by binding active TGF-beta as well as reducing plasmin activity, human vascular smooth muscle cells were cultured in the presence of Lp(a). These cells had a population doubling time of 47+/−3 hours. Addition of plasmin was able to overcome the population doubling time reducing effect of Lp(a) and reduce the cell number to control levels, with the population doubling time increased to 97+/−4 hours.

The role of plasmin in the pathway was confirmed by studies in which inhibitors of plasmin activity were added to human vascular smooth muscle cells. Like Lp(a), these protease inhibitors increased cell number. Aprotinin, for example, decreased the population doubling time from 82+/−4 hours in control cultures to 48+/−5 hours, and alpha2-antiplasmin decreased the population doubling time to 45+/−2 hours. 500 nM Lp(a) and aprotinin addition resulted in only a slight additional stimulation of proliferation, with the population doubling time for cultures of this experiment being 45+/−6 hours. Neutralizing antibodies to TGF-beta similarly decreased population doubling time in vascular smooth muscle cells (see, for example, Example 1). In summary, Lp(a), plasmin inhibitors and neutralizing antibody to TGF-beta stimulate proliferation of vascular smooth muscle cells, while plasmin nullifies the growth stimulation of Lp(a). These results support the theory that the mode of action of Lp(a) and apo(a) is the competitive inhibition of plasminogen activation.

Experimentation conducted to ascertain the impact of tamoxifen on TGF-beta and vascular smooth muscle cell proliferation is set forth in detail in Example 1. The results of those experiments are summarized below.

1) Addition of tamoxifen decreased the rate of proliferation, with maximal inhibition observed at concentrations above 33 micromolar. 50 micromolar tamoxifen concentrations produced a cell number 96 hours following the addition of serum that was reduced by 66% +/−5.2% (n=3) as compared to cells similarly treated in the absence of tamoxifen.

2) Tamoxifen did not significantly reduce the proportion of cells completing the cell cycle and dividing. Inhibition of vascular smooth muscle cells caused by tamoxifen therefore appears to be the result of an increase in the cell cycle time of nearly all (>90%) of the proliferating cells.

3) Tamoxifen decreases the rate of proliferation of serum-stimulated vascular smooth muscle cells by increasing the time taken to traverse the $G_2$ to M phase of the cell cycle.

4) Tamoxifen decreased the rate of proliferation of vascular smooth muscle cells by inducing TGF-beta activity.

5) Vascular smooth muscle cells produced TGF-beta in response to tamoxifen. Tamoxifen appears to increase TGF-beta activity in cultures of rat vascular smooth muscle cells by stimulating the production of latent TGF-beta and increasing the proportion of the total TGF-beta which has been activated.

6) Tamoxifen, unlike heparin, does not act by releasing TGF-beta from inactive complexes present in serum.

7) TGF-beta1 mRNA was increased by approximately 10-fold by 24 hours after addition of tamoxifen (10 micromolar). This result suggests that the expression of TGF-beta mRNA by the smooth muscle cells will be increased, thereby facilitating decreased proliferation thereof by activated TGF-beta. This mechanism can be exploited using cells incorporating nucleic acids encoding TGF-beta mRNA, which cells are identifiable by persons skilled in the art employing known techniques.

8) Tamoxifen is a selective inhibitor of vascular smooth muscle proliferation with an $ED_{50}$ (a concentration resulting in 50% inhibition) at least 10-fold lower for vascular smooth muscle cells than for adventitial fibroblasts.

Additional experimentation has shown that the addition of Lp(a) or apo(a) substantially reduced the rat vascular smooth muscle cell proliferation inhibitory activity of tamoxifen, with the population doubling time in the presence of tamoxifen and Lp(a) being 42+/−2 hours (as compared to a population doubling time of 55+/−2 hours for tamoxifen alone, and a time of 35+/−2 hours for the control). Also, the presence of Lp(a) reduced the levels of active TGF-beta produced in response to the addition of tamoxifen by about 50-fold. Addition of plasmin to rat vascular smooth muscle cells treated with tamoxifen and Lp(a) resulted in most of the TGF-beta being activated, and proliferation was again slowed (with the population doubling time being 57+/−3 hours). These observations are consistent with the theory that Lp(a) acts by inhibiting TGF-beta activation.

Identification of therapeutic agents (direct or indirect TGF-beta activators or production stimulators) that act to inhibit vascular smooth muscle cell proliferation by the pathway shown in FIG. 1 can be identified by a practitioner in the art by conducting experiments of the type described above and in Example 1. Such experimental protocols facilitate the identification of therapeutic agents useful in the practice of the present invention and capable of one of the following activities:

1) production or activation of TGF-beta;
2) having TGF-beta activity;
3) activation of plasmin;
4) activation of plasminogen; and
5) reduction of Lp(a) or apo(a) level.

Identification of therapeutic agents (direct or indirect TGF-beta activators or production stimulators) that act to inhibit vascular smooth muscle cell proliferation by the pathway shown in FIG. 2 can be identified by a practitioner in the art by conducting experimentation using known techniques that are designed to identify growth factors made by proliferating smooth muscle cells, which growth factors also act on those cells (i.e., autocrine growth factors). Known techniques for rational drug design are then used to screen small molecules for the ability to inhibit the production or activity of such autocrine growth factors. Such experimental protocols facilitate the identification of therapeutic agents useful in the practice of the present invention and capable of one of the following activities:

1) production or activation of TGF-beta;
2) having TGF-beta activity; and
3) inhibit the activity or production of an autocrine growth factor produced by proliferating smooth muscle cells.

Smooth muscle cell proliferation is a pathological factor in myocardial infarctions, atherosclerosis, thrombosis, restenosis and the like. Therapeutic/prophylactic agents of the present invention, including tamoxifen and the like, having at least one of the activities recited above and therefore being capable of inhibiting proliferation of vascular smooth muscle cells, are useful in the prevention or treatment of these conditions. Manipulation of the proliferation modulation pathway for vascular smooth muscle cells to prevent or reduce such proliferation removes or reduces a major component of the arterial lesions of atherosclerosis and the restenosed arteries following angioplasty, for example.

More specifically, chronically maintaining an elevated level of activated TGF-beta reduces the probability of atherosclerotic lesions forming as a result of vascular smooth muscle cell proliferation. Consequently, administration of TGF-beta activators or TGF-beta production stimulators protects against atherosclerosis and subsequent myocardial infarctions that are consequent to coronary artery blockage. Also, substantially increasing the activated TGF-beta level for a short time period allows a recipient to at least partially offset the strong stimulus for vascular smooth muscle cell proliferation caused by highly traumatic injuries or procedures such as angioplasty. Continued lower dose delivery to the traumatized site further protects against restenosis resulting from vascular smooth muscle cell proliferation in the traumatized area.

Tamoxifen, for example, is commercially available from ICI Pharmaceuticals (Macclesfield, England). The prevalent commercially available form is a 10 mg tablet. Such tablets or portions thereof can be employed in the prophylactic and treatment protocols described herein.

Prevention or treatment relating to a traumatized or diseased vascular site, for example, the TGF-beta activators or production stimulators may also be administered in accordance with the present invention using an infusion catheter, such as produced by C.R. Bard Inc., Billerica, Mass., or that disclosed by Wolinsky (7; U.S. Pat. No. 4,824,436) or Spears (U.S. Pat. No. 4,512,762). In this case, a therapeutically/prophylactically effective dosage of the TGF-beta activator or production stimulator will be typically reached when the concentration thereof in the fluid space between the balloons of the catheter is in the range of about $10^{-3}$ to $10^{-12}$M. It is recognized by the present inventors that TGF-beta activators or stimulators may only need to be delivered in an anti-proliferative therapeutic/prophylactic dosage sufficient to expose the proximal (6 to 9) cell layers of the intimal or tunica media cells lining the lumen thereto. Also, such a dosage can be determined empirically, e.g., by a) infusing vessels from suitable animal model systems and using immunohistochemical methods to detect the TGF-beta activator or production stimulator and its effects; and b) conducting suitable in vitro studies.

It will be recognized by those skilled in the art that desired therapeutically/prophylactically effective dosages of a TGF-beta activator or production stimulator administered by a catheter in accordance with the invention will be dependent on several factors, including, e.g.: a) the atmospheric pressure applied during infusion; b) the time over which the TGF-beta activator or production stimulator administered resides at the vascular site; c) the nature of the therapeutic or prophylactic agent employed; and/or d) the nature of the vascular trauma and therapy desired. Those skilled practitioners trained to deliver drugs at therapeutically or prophylactically effective dosages (e.g., by monitoring drug levels and observing clinical effects in patients) will determine the optimal dosage for an individual patient based on experience and professional judgment. In a preferred embodiment, about 0.3 atm (i.e., 300 mm of Hg) to about 5 atm of pressure applied for 15 seconds to 3 minutes directly to the vascular wall is adequate to achieve infiltration of a TGF-beta activator or production stimulator into the smooth muscle layers of a mammalian artery wall. Those skilled in the art will recognize that infiltration of the TGF-beta activator or production stimulator into intimal layers of a diseased human vessel wall will probably be variable and will need to be determined on an individual basis.

While two representative embodiments of the invention relate to prophylactic or therapeutic methods employing an oral dosage for or infusion catheter administration, it will be recognized that other methods for drug delivery or routes of administration may also be useful, e.g., injection by the intravenous, intralymphatic, intrathecal, intraarterial, local delivery by implanted osmotic pumps or other intracavity routes. Administration of TGF-beta activators or production stimulators in accordance with the present invention may be continuous or intermittent, depending, for example, upon the recipient's physiological condition, whether the purpose of the administration is therapeutic or prophylactic and other factors known to skilled practitioners.

In the practice of certain embodiments of the present invention, catheter and other administration routes are preferably conducted using a TGF-beta activator or production stimulator dispersed in a pharmaceutically acceptable carrier that is in liquid phase. Useful pharmaceutically acceptable carriers include generally employed carriers, such as phosphate buffered saline solution, water, emulsions (e.g., oil/water and water/oil emulsions) and wetting agents of various types.

For TGF-beta activators or production stimulators, such as tamoxifen, several exemplary dosing regimens are contemplated, depending upon the condition being treated and the stage to which the condition has progressed. For prophylactic purposes with respect to atherosclerosis, for example, a low chronic dose sufficient to elevate in vivo TGF-beta production is contemplated. An exemplary dose of this type is about 0.1 mg/kg/day (ranging between about 0.1 and about 10 mg/kg/day). Another exemplary dose range is from about 0.01 to about 1000 micrograms/ml. Such low doses are also contemplated for use with respect to ameliorating stenosis following relatively low trauma injury or intervention, such as vein grafts or transplants or organ allografts, for example. No adverse side effects (e.g., nausea as experienced by recipients of higher dose administrations when tamoxifen has been employed in the treatment of breast cancer) are anticipated with respect to these chronic or low dosing regimens.

For prevention of restenosis following angioplasty, an example of a higher trauma injury or intervention resulting in a stronger acute proliferative stimulus to smooth muscle cells, a higher dose would be required. For example, a dosing regimen is contemplated which involves a single "pre-loading" dose (or multiple, smaller pre-loading doses) given before or at the time of the intervention, with a chronic smaller (follow up) dose delivered daily for two to three weeks or longer following intervention. For example, a single pre-loading dose may be administered about 24 hours prior to intervention, while multiple preloading doses may be administered daily for several days prior to intervention. Alternatively, one or more pre-loading doses may be administered about 1–4 weeks prior to intervention. These doses will be selected so as to maximize TGF-beta activator or production stimulator activity, while minimizing induction of synthesis and secretion of extracellular matrix proteins. An exemplary single pre-loading dose is about 50 mg/kg (ranging between about 10 and about 1000 mg/kg), while an exemplary multiple pre-loading individual dose is about 10 mg/kg/day (ranging between about 0.01 and 10 mg/kg/day).

It will be recognized that where the TGF-beta activator or production stimulator is to be delivered with an infusion catheter, the therapeutic dosage required to achieve the desired inhibitory activity can be anticipated through the use of in vitro studies. In a preferred aspect, the infusion catheter may be conveniently a double balloon or quadruple balloon catheter with a permeable membrane. In one representative embodiment, a therapeutically effective dosage of a TGF-beta activator or production stimulator is useful in treating vascular trauma resulting from disease (e.g., atherosclerosis, aneurysm, or the like) or vascular surgical procedures such as angioplasty, atheroectomy, placement of a stent (e.g., in a vessel), thrombectomy, and grafting. Atheroectomy may be performed, for example, by surgical excision, ultrasound or laser treatment, or by high pressure fluid flow. Grafting may be, for example, vascular grafting using natural or synthetic materials or surgical anastomosis of vessels such as, e.g., during organ grafting. Those skilled in the art will recognize that the appropriate therapeutic dosage for a given vascular surgical procedure (above) is determined in in vitro and in vivo animal model studies, and in human preclinical trials.

While two representative embodiments of the invention relate to therapeutic methods employing an oral dosage for or infusion catheter administration, it will be recognized that other methods for drug delivery or routes of administration may also be useful, e.g., injection by the intravenous, intralymphatic, intrathecal, intraarterial, local delivery by implanted osmotic pumps or other intracavity routes. Administration of TGF-beta activators or production stimulators in accordance with the present invention may be continuous or intermittent, depending, for example, upon the recipient's physiological condition, whether the purpose of the administration is therapeutic or prophylactic and other factors known to skilled practitioners.

In the practice of certain embodiments of the present invention, catheter and other administration routes are preferably conducted using a TGF-beta activator or production stimulator dispersed in a pharmaceutically acceptable carrier that is in liquid phase. Useful pharmaceutically acceptable carriers include the generally employed carriers, such as phosphate buffered saline solution, water, emulsions (e.g., oil/water and water/oil emulsions) and wetting agents of various types.

Human vascular smooth muscle cells (VSMC) are more difficult to grow in culture than VSMC derived from other species, such as rat (doubling time for adult human VSMC= 70–85 h; for adult rat VSMC=35 h). Medium conditioned on human VSMC decreased the proliferation of rat VSMC in vitro. Entry of rat VSMC into S phase of the cell cycle was not affected. However, the duration of $G_2$ and/or M phase was extended. Anti-TGF-beta antibody reversed the delayed entry into M phase caused by exposure to human VSMC conditioned medium (HCM). An examination of the HCM showed that 64±12% of the TGF-beta present in the medium was already activated. In contrast, rat VSMC conditioned medium displayed very low levels of latent TGF-beta and no detectable TGF-beta activity. Human VSMC were found to produce t-PA activity in culture. The t-PA leads to an increase in plasmin activity, which in turn activates TGF-beta. This was confirmed by culturing human VSMC in the presence of aprotinin, a plasmin inhibitor. Aprotinin increased the rate of proliferation of human VSMC to almost the same extent as neutralizing anti-TGF-beta antibodies and $\alpha_2$-antiplasmin. Thus, growth of human VSMC in culture is determined by the production of TGF-beta activated by plasmin, which feeds back in an autocrine loop to increase the duration of the cell cycle.

Subcultured human aortic VSMC remain more differentiated in culture than rat aorta VSMC (i.e., they contain higher levels of the smooth muscle-specific isoforms of myosin heavy chain (SM-MHC) and $\alpha$-actin). TGF-beta likely plays a role in maintaining SM-MHC and $\alpha$-actin content, and thus may be responsible for maintaining cells in a more differentiated phenotype. In view of these data, heparin, which is believed to release TGF-beta from inactive complexes in the serum, would be predicted to have little effect on the rate of proliferation of human VSMC, which is already inhibited by endogenous active TGF-beta production. Such observations may explain why human clinical trials of heparin administered after PTCA have failed to demonstrate any beneficial effect.

Freshly dispersed rat aortic VSMC lose SM-MHC and $\alpha$-SM actin as they start to proliferate. After 7 days in culture when the cells reach confluence. When serum is removed, approximately 40% of the VSMC reexpress SM-MHC and $\alpha$-SM actin at levels comparable to those present in freshly dispersed cells. If the cells were subcultured for more than five passages and allowed to reach confluence, less than 1% reexpress SM-MHC even after prolonged serum withdrawal. These cells represent proliferating de-differentiated VSMC.

When primary cultures of rat aortic VSMC are exposed to TGF-beta, the loss of the 204 kD (SM-1) and 200 kD (SM-2) SM-MHC isoforms is substantially inhibited. However, TGF-beta did not induce re-expression of SM-MHC in subcultured cells that have very low levels of this protein. Therefore, TGF-beta can maintain a cell's differentiated state (as defined by SM-MHC content), but cannot induce re-differentiation in a de-differentiated proliferating cell. Since TGF-beta extends the $G_2$ phase of the cell cycle in both primary and passaged VSMC cultures, the data suggest that the pathways that mediate proliferation and differentiation are regulated independently.

Specific markers of both differentiated and proliferating VSMCs have been isolated. Four cell populations were probed using generated cDNAs: (a) freshly dispersed rat aortic cells; (b) freshly dispersed rat aortic VSMC after 7 days in culture (D7 cells); (c) freshly dispersed rat aortic VSMC after subculturing 12 times (S12 cells); and (d) rat fibroblasts. Five classes of gene markers were defined. Class 1 cDNAs were expressed to a similar level in all of the RNAS. Class 2 cDNAs were highly expressed in RNA from freshly dispersed aortic cells, but were barely detectable in D7 or S12 cells and were not detectable in rat fibroblasts. Class 3 cDNAs were expressed at similar levels in freshly dispersed aortic, D7 and S12 cells. Class 4 cDNAs showed higher expression in freshly dispersed aortic and D7 cells than in S12 cells and fibroblasts. Class 5 cDNAs were expressed more strongly in S12 cells than in freshly dispersed aortic cells, D7 cells and fibroblasts. Class 4 genes included $\alpha$-SM actin, $\gamma$-SM actin, SM22$\alpha$, calponin, tropoelastin, phospholamban and CHIP28. In addition, previously defined markers of the differentiated phenotype include SM-MHC, integrin and vinculin. Class 5 genes included matrix Gla (MGP) and osteopontin. When passaged cells were made quiescent by removal of serum, the levels of MGP and osteopontin did not change significantly, indicating that high expression of these two genes occurs in SMC that have undergone proliferation, but does not depend on the cells being in the cell cycle.

Such studies of gene expression provide insight into the processes of de-differentiation that occur during proliferation of VSMC. In situ hybridization analysis of balloon-injured rat carotid arteries suggests that dividing intimal cells present 7 days after injury express high levels of both osteopontin and MGP RNA. In contrast, osteopontin is only weakly expressed in the media of intact rat aorta and carotid arteries. Osteopontin and MGP may play a role in regulating calcification, which can occur rapidly in vascular lesions.

In the course of investigating potential heterogeneity of cells from rat aortas, three groups of VSMC clones have been identified. One group consists of small cells that have an epithelioid or cobblestone morphology and proliferate without the need for added growth factors, suggesting production of an autocrine growth factor(s). The second group consists of intermediate size, spindle shaped cells that grow in a characteristic "hills and valleys" pattern and are dependent on exogenous growth factors. These cells resemble the predominant cell morphology in standard cultures of adult aortic VSMC. The third group consists of large, often multinucleate, cells with limited proliferative capacity. These large cells express high quantities of smooth muscle specific proteins.

All three types of cells could be isolated from neonatal and adult rat aortae. However, aortas from young rats yielded high proportions of the small cell clones, while those from adult rats yielded high proportions of intermediate and large cell clones. Clones of small VSMC can be induced to convert to intermediate sized cells by treatment with TGF-beta. A proportion of these cells, in turn, converts to large cells if plated at low density. The small cells may represent a progenitor cell and the large, non-proliferating cells may represent mature VSMC.

VSMC derived from neonatal rat aortas differ from normal adult VSMC in several ways: (a) they do not require exogenous growth factors for sustained growth; (b) they secrete PDGF-like growth factors; (c) they grow with a characteristic epithelioid morphology; and (d) they express high levels of cytochrome P450IA1, elastin and osteopontin (*J. Biol. Chem.* 266:3981–86, 1991; *Biochem. Biophys. Res. Comm.* 177:867–73, 1991; *Nature* 311:669–71, 1984). After intimal damage, neointimal lesions grow with an epithelioid morphology, secrete a PDGF-like protein and display increased expression of osteopontin in the vascular wall (*Proc. Natl. Acad. Sci. USA* 83:7311–15, 1986). These data are consistent with the presence in vivo of a subpopulation of VSMC that comprises a diminishing proportion of the total cell population with age and which proliferates preferentially.

TGF-beta is released by platelets, macrophages and VSMC at sites of vascular injury. Since VSMC and endothelial cells at the site of vascular injury can synthesize and release t-PA, a local mechanism for activating secreted TGF-beta exists. The level of t-PA activity depends on expression of plasminogen activator inhibitor-1 (PAI-1) which is also synthesized in the vessel wall, and may be up-regulated by TGF-beta. In addition, TGF-beta binds with high affinity to α2-macroglobulin. Such binding renders TGF-beta unable to bind to cell surface receptors for TGF-beta. Polyanionic glycosaminoglycans, such as heparin, are also normally present in the vessel wall, and these moieties can reverse the association of TGF-beta with α2-macroglobulin. The phenotypic state of the VSMC may affect the VSMC response to activated TGF-beta. The phenotypic state of the VSMC may be influenced by their extracellular environment. Accordingly, the biological effects of TGF-beta are subject to a variety of regulatory mechanisms.

TGF-beta inhibits DNA synthesis in rat aortic VSMC stimulated with either PDGF or EGF. In serum stimulated cells, however, TGF-beta has little effect on DNA synthesis.

Instead, TGF-beta exerts its anti-proliferative effect by prolonging the $G_2$ phase of the cell cycle. Likewise, heparin inhibits proliferation of serum-stimulated rat VSMC by extending the $G_2$ phase of the cell cycle. This effect of heparin can be eliminated by anti-TGF-beta antibody. These observations suggest that the anti-proliferative effect of heparin on VSMC in vitro and possibly in vivo may be exerted through the release of TGF-beta.

When VSMC are dispersed in cell culture, they lose contractile proteins and modulate to a "synthetic" phenotype as they proliferate. The majority of VSMC in atheromatous plaques appear to have this synthetic phenotype also. Since loss of smooth muscle-specific proteins occurs spontaneously in cell culture in the absence of mitogens where no proliferation occurs, this phenotypic change is not attributable to mitogenic stimulation, but rather to removal of the cells from their extracellular matrix. The matrix contains large quantities of collagen and glycosaminoglycans that may maintain VSMC in a contractile state. TGF-beta does not exert its anti-proliferative effect through inhibition of phenotypic modulation, however, since it is effective at slowing proliferation of passaged cells that can no longer express contractile proteins. Thus, TGF-beta displays the independent properties of (1) maintaining differentiated adult VSMC in the contractile phenotype; (2) causing maturation of small VSMC to intermediate size, spindle-shaped VSMC; and (3) inhibiting VSMC proliferation regardless of phenotype. Change from a contractile to synthetic phenotype is not obligatory for proliferation.

Cultured VSMC synthesize and secrete large quantities of extracellular matrix proteins. TGF-beta enhances production of extracellular matrix proteins, which favors maintenance of the synthetic phenotype in cells that have been allowed to modulate. In addition, TGF-beta increases expression of numerous protease inhibitors, which also increase accumulation of extracellular matrix proteins.

In hypertension, there is increased thickness of the vessel media, with a consequent decrease in maximum lumen diameter, leading to increased vascular resistance. The increased thickness of the vessel media is due to growth of VSMC within the media. In large conductance vessels, such as the aorta, the VSMC growth is believed to be attributable primarily to VSMC hypertrophy (i.e., enlargement of the cell without proliferation). In hypertensive animals, these vessels display an increased incidence of polyploid cells within the aortic media. In resistance vessels, such as the mesenteric arteries, however, VSMC proliferation may contribute to the increased thickness of the vessel media. Previously, VSMC growth in hypertension was believed to result from elevated blood pressure. Current data suggest that increased vascular tone and VSMC hypertrophy and/or hyperplasia may be caused independently by a common stimulus. For instance, under certain circumstances, the vasoconstrictor peptide AII may be mitogenic for VSMC. Further, VSMC stimulated with AII also synthesize TGF-beta. Thus, any mitogenic effect of AII might be inhibited by TGF-beta, with the net effect of AII stimulation being arrest in $G_1$ and hypertrophy without proliferation. AII may induce activation of TGF-beta by stimulating expression of t-PA by VSMC.

The VSMC involved in hypertension remain within the media of the vessel and are surrounded by a heparin-containing extracellular matrix. Therefore, any TGF-beta produced is freely available and will maintain VSMC in a contractile state.

In obliterative vascular disease, such as atherosclerosis, VSMC migrate from the media and proliferate in the intima. There they secrete extracellular matrix proteins and form a lipid-rich plaque that encroaches on the vascular lumen. This process is similar to, but slower than, the process that occurs following PTCA, leading to restenosis. Such inappropriate intimal VSMC proliferation also occurs in vascular bypass grafts and the arteries of transplanted organs, leading to graft occlusion and organ failure, respectively. In atherosclerosis, the VSMC involved in the lesion are generally of the synthetic phenotype and localized in the intima, in contrast to the VSMC involved in hypertension.

For medial VSMC involved in atherosclerosis, VSMC migration is accompanied by an increase in synthesis and secretion of matrix proteins and by proliferation. TGF-beta may reduce or prevent the VSMC proliferative response to mitogens and/or may induce synthesis and secretion of extracellular matrix proteins. The effect of TGF-beta in this case would be reduction of cellularity and increase of the matrix component of an atherosclerotic plaque.

Alternatively, VSMC in the intima may arise from a population of neonatal-like VSMC that are capable of migration and preferential proliferation following vascular injury. This intimal phenotype may be either induced or selected in response to vessel injury. When these cells are exposed to TGF-beta, the neonatal-like, small cell phenotype should convert into intermediate sized, spindle-shaped cells that no longer produce an autocrine growth factor. Thus, cells of the intermediate size should have a decreased tendency to proliferate. Over time, a portion of this intermediate sized population of cells would convert to the large, non-proliferative VSMC phenotype.

If VSMC are producing autocrine TGF-beta, tamoxifen has minimal or no further inhibitory effect on VSMC proliferation. Moreover, these TGF-beta-producing VSMC exhibit responses to mitogenic stimuli that may differ from those of VSMC that are not producing TGF-beta. Such data provides further evidence of a complex interaction between the elements that are likely involved in atherosclerosis and vascular injury or trauma.

Transgenic mice that express the human apo(a) gene are useful tools for studying TGF-beta activation, VSMC proliferation and vascular lesions that mimic early human atherosclerotic lesions. In these mice, the apo(a) accumulates in focal regions in the luminal surface of vessel walls. These foci of apo(a) inhibit plasminogen activation, which leads to a decrease in production of plasmin. A low local concentration of plasmin results in reduced activation of TGF-beta. This inhibition of TGF-beta activation is greatest at sites of highest apo(a) accumulation. Further, these effects are observed whether the transgenic mice are fed a normal diet or a lipid-rich diet. Serum levels of activated TGF-beta correlate with the immunofluorescence determinations performed on tissue sections. Osteopontin, a marker of activated VSMC, co-localized with focal apo(a) accumulation and regions of very low TGF-beta activation.

In general, atherosclerosis is a cardiovascular disease in which the vessel wall is remodeled, compromising the lumen of the vessel. The atherosclerotic remodeling process involves accumulation of cells, both smooth muscle cells and monocyte/macrophage inflammatory cells, in the intima of the vessel wall. These cells take up lipid, likely from the circulation, to form a mature atherosclerotic lesion. Although the formation of these lesions is a chronic process, occuring over decades of an adult human life, the majority of the morbidity associated with atherosclerosis occurs when a lesion ruptures, releasing thrombogenic debris that rapidly occludes the artery. When such an acute event occurs in the coronary artery, myocardial infarction can ensue, and in the worst case, can result in death.

The formation of the atherosclerotic lesion can be considered to occur in five overlapping stages. Each of these processes can be shown to occur in man and in animal models of atherosclerosis, but the relative contribution of each to the pathology and clinical significance of the lesion is unclear.

1. MIGRATION. In a healthy vessel, most or all of the smooth muscle cells (SMC) are contained in the vessel media. The appearance of SMC in the enlarged intima during lesion formation must therefore require migration of the SMC from the media to the intima of the vessel. Inhibition of this SMC migration would significantly alter the nature of the lesion, and may ameliorate the pathology associated with lesion formation.

2. LIPID ACCUMULATION. Medial SMC in healthy vessel walls do not significantly accumulate lipid. However, intimal SMC have an increased capacity for lipid uptake and storage. When exposed to elevated levels of circulating lipid (particularly low density lipoprotein; LDL), SMC may become saturated with fatty lipid and die. The accumulation of lipid is necessary for the progression of the lesion to clinical significance, since it forms the thrombogenic necrotic core of the lesion. Inhibition of lipid accumulation in the SMC should significantly reduce or prevent lesion formation and/or progression, thus reducing or preventing atherosclerosis and resultant myocardial infarction.

3. RECRUITMENT OF INFLAMMATORY CELLS. Human lesions contain many macrophage-derived cells. The process of recruitment, the function of these cells, and their contribution to pathology are unclear. An oversimplified mechanism suggests that macrophages are attracted to the lipid accumulating in the lesion, in order to remove the lipid from the vessel wall. While inhibition of recruitment of macrophage-derived cells might reduce lesion pathology, it may also speed progression to the lipid-filled, rupture-prone state.

4. PROLIFERATION. Intimal SMC accumulation is accompanied by medial thinning in many cases. Therefore, total SMC number may not increase significantly at the lesion site. Furthermore, the chronic nature of atherosclerosis makes it difficult to detect stimulation of proliferation in these lesions. Data obtained from transgenic apo(a) mice suggest that apo(a) may stimulate SMC proliferation. However, evidence that SMC hyperplasia is a major contributor to atherosclerosis is lacking. Thus, the ultimate effect that inhibition of apo(a) has on atherosclerosis is dependent on the contribution of SMC proliferation to initiation or progression of an atherosclerotic plaque.

5. EXTRACELLULAR MATRIX DEPOSITION. Atherosclerotic lesions are also rich in extracellular matrix (ECM), and in particular, collagen fibers. Increased ECM synthesis may increase plaque stability. Early plaque rupture, leading to myocardial infarction, may be associated with low ECM deposition and resultant weakening of the fibrous cap that overlays the necrotic, lipid-rich core of the lesion.

Accordingly, atherosclerosis involves the complex interplay of various processes, some of which may be yet unidentified. Targeting a single process in an effort to reduce or prevent atherosclerosis depends on knowledge of the relative contribution of each process to the manifested pathology. For these reasons, a coordinated, therapeutic strategy is preferred. An exemplary strategy involves inhibition of SMC migration, lipid accumulation and proliferation, with possible beneficial effects of increasing ECM deposition.

A diagnostic assay for identifying patients at risk for atherosclerosis, and therefore for identifying suitable candidates for therapy, finds use within this invention. In addition, this diagnostic assay provides a means to monitor patients that are being treated for atherosclerosis. In one format, a sandwich ELISA for determining total TGF-beta, ELISA plates are coated with a rat antibody that binds both latent and active TGF-beta. Patient sera are incubated with these ELISA plates, then the plates are washed to remove unbound components of the patients' sera. Rabbit anti-TGF-beta antibody, capable of binding both latent and active TGF-beta, is then added to the plates and incubated. The plates are then washed to remove unbound antibody, and peroxidase-labeled anti-rabbit IgG is added. After incubation and washing, the plates are exposed to the chromogenic substrate, orthophenylenediamine. The presence of total TGF-beta in patients' sera is then determined calorimetrically at $A_{492}$ by comparison to a standard curve. In patients treated with an agent that modifies TGF-beta, a pretreatment determination of TGF-beta can be compared with post-treatment timepoints to monitor treatment results and effectiveness.

In an alternate format, TGF-beta type II receptor extracellular domain, which recognizes the active form of TGF-beta, is coated onto ELISA plates. Patient sera are added to the plates, and processed as above. This assay measures active TGF-beta present in sera.

In another alternate format, fluorescent-labeled anti-TGF-beta antibody or TGF-beta type II receptor extracellular domain is used in place of peroxidase labeled second antibody to detect the presence of TGF-beta in patients' sera. In yet another alternate format, anti-TGF-beta antibody or TGF-beta type II receptor extracellular domain is labeled with a radioactive moiety capable of detection by standard means. These latter two assays may be performed in an ELISA format, with or without using the additional anti-TGF-beta antibody described above. In addition, these latter two assays are amenable to other automated or non-automated assay and detection methods.

The invention will be better understood by making reference to the following specific examples.

EXAMPLE 1

Impact of Tamoxifen on Vascular Smooth Muscle Cells and the Relationship thereof to TGF-Beta Production and Activation Cell culture, DNA synthesis assay and cell counting. Rat vascular smooth muscle cells were cultured after enzymatic dispersion of the aortic media from 12–17 week old Wistar rats as described in Grainger et al., Biochem. J., 277: 145–151, 1991. When the cells reached confluence (after about 6 days) the cells were released with trypsin/EDTA (available from Gibco) and diluted 1:2 in Dulbecco's modification of Eagle's medium (DMEM; available from ICN/Flow) supplemented with 100 U/ml penicillin and 10% fetal calf serum (FCS). The cells were then replated on tissue culture plastic (available from ICN/Flow) at approximately $1 \times 10^4$ cells/cm$^2$. The cells were subcultured repeatedly in this way when confluence was attained (about every 4 days), and the cells were used between passages 6 and 12.

Rat adventitial fibroblasts were cultured as described in Grainger et al., Biochem. J., 283: 403–408, 1992. Briefly, the aortae were treated with collagenase (3 mg/ml) for 30 minutes at 37° C. The tunica adventitia was stripped away from the media. The adventitia was dispersed for 2 hours in elastase (1 mg/ml) and collagenase (3 mg/ml) dissolved in medium M199 (available from ICN/Flow). The cells were then spun out (900×g, 3 minutes), resuspended in DMEM+10% FCS and plated out at $8 \times 10^4$ cells/cm$^2$ on tissue culture plastic. When the cells reached confluence (after about 10 days), they were subcultured as described for vascular smooth muscle cells. Adventitial fibroblasts were subcultured every 3 days at 1:3 dilution and used between passages 3 and 9.

DNA synthesis was assayed by [$^3$H]-thymidine incorporation as described in Grainger et al., Biochem. J., 277:145–151, 1991. Vascular smooth muscle cells were subcultured, grown in DMEM+10% FCS for 24 hours, made quiescent in serum-free DMEM for 48 hours and restimulated with 10% FCS at "0" hours. [$^3$H]-thymidine (5 microcuries/ml; available from Amersham International) was added 12 hours after restimulation and the cells were harvested after 24 hours. DNA synthesis by adventitial fibroblasts was determined similarly, except that the cells were made quiescent in serum-free DMEM for 24 hours.

Cells were prepared for counting by hemocytometer from triplicate culture dishes as described in Grainger et al., Biochem. J., 277:145–151, 1991. Cells were also counted by direct microscopic observation of gridded culture dishes. The grids were scored into the plastic on the inner surface, so that the cells could not migrate into or out of the area being counted during the experiment. Cells in each of four squares in two separate wells were counted at each time point. All cell counting experiments were repeated on at least three separate cultures.

A stock solution of tamoxifen (5 mM; available from ICI Pharmaceuticals) was made up in 10% ethanol (EtOH) and diluted in DMEM and 10% FCS to give the final concentration. The effects of each tamoxifen concentration were compared with the effects observed in control wells containing the same final concentration of the ethanol vehicle. Recombinant TGF-beta (available from Amersham International) was dissolved in 25 mM Tris/Cl to give a 5 microgram/ml stock solution and sterile filtered through a Spinnex Tube (such as a Centrex Disposable Microfilter Unit available from Rainin Instrument Company, Inc., Woburn, Mass.). Neutralizing antiserum to TGF-beta (BDA19; available from R & D Systems) was reconstituted in sterile MilliQ water (available from Millipore Corporation, Bedford, MA). At 10 micrograms/ml, this antibody completely abolished the activity of 10 ng/ml recombinant TGF-beta on subcultured (8th passage) vascular smooth muscle cells.

Assays for TGF-Beta. The TGF-beta activity present in medium conditioned on various cells was determined by DNA synthesis assay on mink lung endothelial (MvLu) cells; a modification of the assay described in Danielpour et al., J. Cell. Physiol., 138: 79–83, 1989. MvLu cells were subcultured at 1:5 dilution in DMEM+10% FCS. After 24 hours, the medium was replaced with the conditioned medium to be tested in the absence or presence of the neutralizing antiserum to TGF-beta at 10 micrograms/ml. DNA synthesis during a 1 hour pulse of [$^3$H]-thymidine (5 microcuries/ml) was determined 23 hours after addition of the test medium. TGF-beta activity was calculated as the proportion of the inhibition of DNA synthesis which was reversed in the presence of neutralizing antibody, using a standard curve to convert the inhibition values into quantities of TGF-beta. The TGF-beta1 standards and conditioned media both contained 10% FCS in DMEM.

The total latent and active TGF-beta present was determined by a sandwich ELISA. Maxisorb 96-well ELISA plates (available from Gibco) were coated with neutralizing antiserum against TGF-beta (BDA19; available from R & D Systems) at 2 micrograms/cm$^2$ in phosphate buffered saline (PBS) overnight at room temperature. The plates were washed between each step with tris-buffered saline containing 0.1% Triton X-100 (available from Sigma Chemical Company). The plates were incubated with samples for 2 hours, with a second antibody to TGF-beta (BDA5; available from R & D Systems) at 0.1 micrograms/ml for 2 hours, with anti-rabbit IgG peroxidase-conjugated antibody (available from Sigma Chemical Co.) for 1 hour, and with the chromogenic substrate o-phenylenediamine (Sigma), made up according to manufacturer's instructions, for 15 minutes. Absorbances at 492 nm were converted into quantities of TGF-beta protein using a standard curve. Both conditioned media and standards were assayed in the presence of 10% FCS in DMEM. This assay was linear for TGF-beta concentrations in the range from 0.1 ng/ml to 20 ng/ml in the presence of 10% FCS in DMEM.

RNA Preparation and Northern Analysis. Total cytoplasmic RNA was isolated from cultured vascular smooth muscle cells as described in Kemp et al., Biochem. J., 277: 285–288, 1991. Northern analysis was performed by electrophoresis of total cytoplasmic RNA in 1.5% agarose gels in a buffer containing 2.2M formaldehyde, 20 mM 3-(N-morpholino)propanesulfonic acid, 1 mM EDTA, 5 mM sodium acetate and 0.5 micrograms/ml ethidium bromide. The integrity of the RNA was checked by visualizing the gel under UV illumination prior to transfer onto Hybond N (available from Pharmacia LKB) as specified by the manufacturer. Filters were hybridized as described in Kemp et al., Biochem. J., 277: 285–288, 1991, using a [$^{32}$P]-oligolabeled mouse TGF-beta1 probe corresponding to amino acids 68–228 in the precursor region of the TGF-beta1 polypeptide as set forth in Millan et al., *Development*, 111: 131–144.

Results. Vascular smooth muscle cells from the aorta of adult rats proliferate with a cell cycle time of approximately 35 hours in DMEM+10% FCS (see, for example, Grainger et al., *Biochem. J.*, 277: 145–151, 1991). Addition of tamoxifen decreased the rate of proliferation with maximal inhibition at concentrations above 33 micromolar. 50 micromolar tamoxifen concentrations produced an increase in cell number (96 hours following the addition of serum) that was reduced by 66% +/–5.2% (n=3). The slower rate of proliferation was hypothesized to stem from a complete blockage of proliferation for a proportion of the vascular smooth muscle cells or from an increase in the cell cycle time of all of the cells. To distinguish between these possibilities, the proportion of the cells passing through M phase and the time course of entry into cell division were determined.

Quiescent vascular smooth muscle cells were stimulated with DMEM+10% FCS in the absence or presence of 33 micromolar tamoxifen, with the cell number being determined at 8 hour intervals by time lapse photomicroscopy. In the presence of ethanol vehicle alone, more than 95% of the vascular smooth muscle cells had divided by 40 hours, whereas there was no significant increase in cell number in the presence of tamoxifen until after 48 hours. By 64 hours, however, more than 90% of the cells had divided in the presence of tamoxifen. The time taken for 50% of the cells to divide after stimulation by serum was increased from 35+/–3 hours (n=7) to 54+/–2 hours (n=3) by 33 micromolar tamoxifen. Since tamoxifen did not significantly reduce the proportion of cells completing the cell cycle and dividing, inhibition of vascular smooth muscle cells caused by tamoxifen appears to be the result of an increase in the cell cycle time of nearly all (>90%) of the proliferating cells.

To determine whether tamoxifen increased the duration of the cell cycle of vascular smooth muscle cells by increasing the duration of the $G_0$ to S phase, the effect of tamoxifen on entry into DNA synthesis was analyzed. Tamoxifen at concentrations up to 50 micromolar did not significantly affect the time course or the proportion of cells entering DNA synthesis following serum stimulation of quiescent vascular smooth muscle cells (DNA synthesis between 12 hours and 24 hours after stimulation was measured by [$^3$H]-thymidine incorporation: control at 17614+/–1714 cpm; 10 micromolar tamoxifen at 16898+/–3417 cpm; and 50 micromolar tamoxifen at 18002+/–4167 cpm). Since the duration of S phase is approximately 12 hours (unpublished data), tamoxifen does not appear to have significantly impacted the time course of entry into DNA synthesis. These results therefore imply that tamoxifen decreases the rate of proliferation of serum-stimulated vascular smooth muscle cells by increasing the time taken to traverse the $G_2$ to M phase of the cell cycle.

Based upon these results, it appeared that tamoxifen exhibited effects similar to those previously described for TGF-beta (see, for example, Assoian et al., *J. Cell. Biol.*, 109: 441–448, 1986) with respect to proliferation of subcultured vascular smooth muscle cells in the presence of serum. Tamoxifen is known to induce TGF-beta activity in cultures of breast carcinoma cell lines as described, for example, in Knabbe, et al., *Cell*, 48: 417–425, 1987. Consequently, experimentation was conducted to determine whether tamoxifen decreased the rate of proliferation of vascular smooth muscle cells by inducing TGF-beta activity. When quiescent vascular smooth muscle cells were stimulated with 10% FCS in the presence of 50 micromolar tamoxifen and 10 micrograms/ml neutralizing antiserum against TGF-beta, the cells proliferated at the same rate as control cells in the presence of ethanol vehicle alone.

To confirm that the vascular smooth muscle cells produced TGF-beta in response to tamoxifen, such cells were treated with tamoxifen for 96 hours in the presence of 10% FCS. The conditioned medium was then collected and TGF-beta activity was determined by the modified mink lung epithelial (MvLu) cell assay described above. Tamoxifen increased the TGF-beta activity in the medium by >50-fold. Addition of tamoxifen (50 micromolar) in fresh DMEM+10% FCS to the MvLu cells had no effect on DNA synthesis, demonstrating that tamoxifen did not induce production of active TGF-beta by the MvLu cells.

TGF-beta is produced as a latent propeptide which can be activated outside the cell by proteases such as plasmin. To determine whether tamoxifen increased TGF-beta activity by promoting the activation of latent TGF-beta or by stimulating the production of the latent propeptide which was subsequently activated, the total latent plus active TGF-beta present in the conditioned medium was determined by sandwich ELISA as described above. After 96 hours in the presence of tamoxifen (50 micromolar), the total TGF-beta protein present was increased by approximately 4-fold. Furthermore, the proportion of the TGF-beta present in active form was increased from <5% in the medium conditioned on vascular smooth muscle cells in the presence of ethanol vehicle alone to approximately 35% in the medium conditioned on cells treated with tamoxifen. Thus, tamoxifen appears to increase TGF-beta activity in cultures of rat vascular smooth muscle cells by stimulating the production of latent TGF-beta and increasing the proportion of the total TGF-beta which has been activated.

Heparin increases TGF-beta activity in medium conditioned on vascular smooth muscle cells (unpublished data). The mechanism of action of heparin in this regard appears to involve the release of TGF-beta from inactive complexes present in serum, because pretreatment of serum with heparin immobilized on agarose beads is as effective as direct addition of free heparin to the cells. To determine whether tamoxifen acts to release TGF-beta from sequestered complexes in serum which are not immunoreactive in the ELISA assay, 10% FCS+DMEM was treated with 50 micromolar tamoxifen for 96 hours at 37° C. in the absence of cells. Medium treated in this way contained similar levels of TGF-beta protein and activity to untreated medium. It appears, therefore, that tamoxifen, unlike heparin, does not act by releasing TGF-beta from inactive complexes present in serum.

The content of TGF-beta1 mRNA was also analyzed by Northern analysis at various time points after addition of tamoxifen. Subcultured rat vascular smooth muscle cells (6th passage in exponential growth) in the absence or presence of ethanol vehicle alone contain very little MRNA for TGF-beta1. By 24 hours after addition of tamoxifen (10 micromolar), TGF-beta1 mRNA was increased approximately 10-fold.

Although TGF-beta decreases the rate of proliferation of vascular smooth muscle cells, it does not affect the rate of proliferation of fibroblasts. Tamoxifen at concentrations of up to 50 micromolar did not reduce the rate of proliferation of subcultured adventitial fibroblasts. Tamoxifen is therefore a selective inhibitor of vascular smooth muscle proliferation with an $ED_{50}$ at least 10-fold lower for vascular smooth muscle cells than for adventitial fibroblasts.

EXAMPLE 2

Heparin Effect on VSMC Proliferation and Differentiation

Heparins. An unfractionated, high molecular weight, anti-coagulant pig mucosal heparin, fragments of heparin devoid of anticoagulant activity, and fragments of heparin with anticoagulant activity were tested. In addition, heparin coupled to agarose beads (Sigma Chemical Co., St. Louis, Mo.) was examined (see also Grainger et al., *Cardiovascular Res.* 27:2238–47, 1993).

Effect on proliferation. Freshly dispersed rat VSMC, prepared as in Example 1, were cultured in medium containing serum (as in Example 1) in the presence or absence of heparin. the cells were counted at intervals. Depending on the heparin used, the increase in cell number at 144 hours (when control cells enter stationary phase) was reduced by between 27±4.2% and 76±3.2% (p<0.0005 compared with cell number in control wells for all heparins tested). Although the effects of the heparins at 100 µg/ml were similar, there was a trend to greater effectiveness with increasing molecular size. The four heparins of 20 kD or above inhibited proliferation by 60–76%, and the four heparins of 12.6–3 kD inhibited proliferation by 27–45%.

Entry into cell cycle phases. Heparin had no effect on the entry of cells into S phase, as determined by growing the cells in the presence of 10 µM bromodeoxyuridine from 0–72 h. Similar results were obtained when the cells were pulse-labeled with [$^3$H]-thymidine.

The proportion of cells completing mitosis in the presence or absence of heparin was determined. Defined fields of cells were photographed at eight hour intervals by time lapse microscopy of gridded culture dishes. The grids were scored into the plastic on the inner surface so that the cells could not migrate into or out of the area being counted. In the absence of heparin, 92±1% of primary cells divided by 60 h, but there was no detectable cell division in the presence of heparin until 72 h. By 88 h, however, 96±2% of the cells had divided in the presence of heparin. In the presence or absence of heparin, the time to complete mitosis was less than 3 h. The total cell cycle times in the presence and absence of heparin were determined. The data showed that the major effect of heparin was to extend selectively the duration of $G_2$ to M phase of the cell cycle.

The concentration of heparin required to inhibit S phase entry decreased as the serum concentration was reduced. This observation is consistent with the removal by heparin of components of serum required for progression to S phase.

Heparin and TGF-beta. To determine whether TGF-beta mediated the effects of heparin, anti-TGF-beta antibody (10 µg/ml; R&D Systems) was added. Anti-TGF-beta antibody alone had no effect on VSMC proliferation stimulated by 10% FCS. This antibody completed reversed the inhibition of VSMC proliferation observed when cells were incubated in the presence of heparin. Heparin coupled to agarose beads at an extracellular concentration of 100 µg/ml was as effective as free heparin (100 µg/ml) at inhibiting VSMC proliferation. Agarose beads alone at the same concentration had no effect. These results are consistent with extracellular action of heparin on VSMC to inhibit proliferation. Further cell cycle studies indicated that heparin must be present within the first 12 hours of $G_1$ to inhibit VSMC proliferation.

Heparin and smooth muscle-specific myosin heavy chain expression. Previous studies demonstrated that primary VSMC in culture lose both the 204 kD (SM-1) and the 200 kD (SM-2) isoforms of SM-MHC, whether the VSMC are cultured in serum or in serum-free medium onto fibronectin. In primary cultures stimulated by serum, 100 µg/ml heparin substantially inhibited the loss of both SM-1 and SM-2 proteins in all cells, as assayed by direct immunoperoxidase staining or Western blotting (*Cell Tissues Res.* 257:1137–39, 1989; *Biochem. J.* 277:145–51, 1991). If the cells were plated in serum-free medium onto fibronectin, the normal loss of SM-1 and MS-2 proteins was unaffected by the presence of heparin. The effect of heparin in preventing the de-differentiation of primary VSMC in serum was completely reversed by the addition of anti-TGF-beta antibody (10 µg/ml), indicating that this heparin effect was also mediated by TGF-beta-like activity. Although heparin prevented the loss of smooth muscle-specific myosin heavy chain from primary VSMC in the presence of serum, it did not promote its reexpression. Moreover, heparin did not promote reexpression of SM-MHC in subcultured cells that exhibit very low levels of this protein. Thus, the effects of heparin and TGF-beta on the expression of SM-MHC in primary VSMC are similar.

EXAMPLE 3

Comparison of Enzyme-Dispersed and Explant-Derived Human VSMC

Materials. Collagenase (C-0130), elastase (E-0258), anti-rabbit IgG peroxidase-conjugated antibody, the chromogenic substrate orthophenylenediamine, and streptomycin sulfate were obtained from Sigma. Tamoxifen (free base) was purchased from Aldrich. Dulbecco's modified Eagle's Medium (D-MEM) and medium M199 were purchased from Flow Laboratories. 6-[$^3$H]-thymidine and the cell proliferation kit were obtained from Amersham International. Anti-TGF-beta antibodies (BDA19 and BDA47) were purchased from R&D Systems. EGF, PDGF-AA and PDGF-BB were obtained from Bachem, and were dissolved in filter-sterilized 25 mM Tris-HCl, pH 7.5, containing 1% fatty acid-free bovine serum albumin (BSA). Basic fibroblast growth factor and insulin-like growth facter 1 (N-mer) were obtained from Bachem and dissolved in sterile MilliQ water. Antiotensin II and endothelin 1 were obtained from Sigma and dissolved in sterile MilliQ water. TGF-beta (0.5 µg, lyophilized solid) was purchased from Peninsula, dissolved in 5 mM HCl to yield a 5 µg/ml stock, and diluted with PBS+0.2% BSA.

Human aortic VSMC cultures. Adult human VSMC were obtained from 6 transplant donors (either sex, age range from 3 to 54 years) using the enzyme dispersal or explant technique. In one case, the same donor (a 24 year old male) was used to establish both an enzyme-dispersed (ED) and explant-derived (EX) cell culture. Prior to enzyme-dispersion or explanting treatment, human aortas were obtained within 18 h of death. The endothelium layer was removed with a scalpel blade and strips of smooth muscle cells (tunica media) were removed with forceps and chopped into small pieces (1 mm$^3$).

ED Cultures. The aortic pieces were washed once with serum-free Hanks Balanced Salt Solution, then enzyme-dispersed with collagenase and elastase, as described in Example 1. The cells were plated at an initial density of 1.5×10$^5$ cells/cm$^2$ and incubated in a humidified atmosphere at 37° C. in 5% $CO_2$ in air. The cells were subcultured every 6–7 days (at stationary phase) by releasing them with trypsin/EDTA and diluting them 1:1.5 in D-MEM+10% FCS. Subcultured ED cells were cultured with D-MEM+20% FCS 24 h after plating, and thereafter at 48 h intervals.

EX Cultures. The aortic pieces were washed once with D-MEM+10% FCS, resuspended in a small volume of fresh D-MEM+10% FCS, and transferred to culture flasks or Petri dishes. The pieces were allowed to sediment onto the plastic and were evenly distributed (≈4 pieces/cm$^2$). Cells started to grow out from the explants after 3–7 d in culture. The aortic pieces were removed during the third week in culture, and the cells adhering to the plastic were allowed to grow to confluence for a further week. The cells were then subcultured every 4–5 days by releasing them with trypsin/EDTA and diluting them 1:2 in D-MEM+10% FCS. Subcultured cells were incubated with fresh D-MEM+20% FCS as described for ED cultures.

ED and EX subcultures were used between passage 5–20.

Cell counting, DNA synthesis assays and assays for total and active TGF-beta were performed as described in Example 1.

Results.

ED and EX cultures prepared from the aorta of a single individual displayed distinct morphologies and growth characteristics. The EX culture proliferated much more rapidly than the ED culture. After 6 weeks of subculturing the ED and EX culture whenever confluence was attained, the total yield of cells was 4 fold higher per g wet weight of aorta in the EX culture than the ED culture. The ED culture had a longer population doubling time in D-MEM+20% FCS (71±5 h) than the EX culture (35±2 h).

The VSMC in the EX culture were spindle-shaped and grew to confluence with a characteristic "hills and valleys" pattern at confluence. The EX culture VSMC reached stationary phase at a high saturation density (2.0–4.0×$10^4$ cells/$cm^2$). In contrast, the VSMC in the ED culture had a stellate morphology with numerous long cytoplasmic projections. They reached stationary phase at a low saturation density (0.7–2.0×$10^4$ cells/$cm^2$) without reaching monolayer coverage of the substrate. The VSMC in the ED culture contained high levels of both SM-MHC and a-actin, while the VSMC in the EX culture contained much lower levels of both of these protein markers.

The longer population doubling time of human ED cultures compared to ED cultures from the rat aorta is due to autocrine production of active TGF-beta. These human ED cultures produced 15.2±1.6 ng/ml total TGF-beta protein, of which 64±12% was in the active form. In contrast, the human EX cultures did not produce detectable amounts of TGF-beta. Medium conditioned for 48 h on EX cultures during exponential growth contained <1 ng/ml total TGF-beta. When TGF-beta production was compared using ED and EX cultures obtained from the same donor, the ED culture produced 8.5 ng/ml total TGF-beta, of which 57% was in the active form. The corresponding EX culture produced <1 ng/ml total TGF-beta protein.

Exogenous TGF-beta (10 ng/ml) was added to EX cultures 24 h after subculturing and cell number was determined at 24 h intervals. After 96 h in the presence of exogenous TGF-beta, the increase in cell number was inhibited by 34±2%. The population doubling time of the EX cultures increased from 32±1 h to 42±3 h in the presence of exogenous TGF-beta.

Because the addition of exogenous TGF-beta extended the population doubling time of EX cultures by less than 12 h, TGF-beta activity alone cannot account for the difference in population doubling time between the ED and EX cultures. Therefore, the fraction of cells that entered DNA synthesis in a 6 day period was compared using bromodeoxyuridine incorporation with a cell proliferation kit. The proportion of EX culture nuclei demonstrating bromodeoxyuridine incorporation after a 6 day pulse was 86±4%, but for ED culture cells was 48±4%. Therefore, the population doubling time of ED cultures was further increased over that of EX cultures, because less of the ED cells than the EX cells were cycling in the presence of D-MEM+20% FCS.

Tamoxifen (TMX) inhibits proliferation of rat ED VSMC by inducing TGF-beta production with a half-maximal inhibition of proliferation at 2–5 $\mu$M TMX. Because human ED cultures already produce autocrine TGF-beta, the addition of TMX would not be expected to reduce the rate of VSMC proliferation further. To confirm this prediction, various concentrations of TMX (1 nM to 100 $\mu$M) or ethanol vehicle only (20 ppm to 0.2%) were added to the human VSMC for 96 h, and the cell number was determined by cell counting. Concentrations of TMX >33 $\mu$M caused cell death, but concentrations below 10 $\mu$M did not affect the rate of proliferation.

EX cultures of human VSMC did not produce autocrine TGF-beta, so TMX would be predicted to inhibit VSMC proliferation. Concentrations of >33 $\mu$M TMX caused cell death in human EX cultures, as observed with human ED cultures. The half-maximal inhibitory dose for EX cultures was 30–100 nM TMX. At 5 $\mu$M TMX, the increase in cell number in human EX cultures was inhibited 33±8%.

To confirm these observations, quiescent EX cultures were restimulated and cultured for 96 h in D-MEM+20% FCS containing TMX (0.5 $\mu$M) in the presence or absence of anti-TGF-beta antibody (25 $\mu$g/ml). The increase in cell number in the presence of TMX alone was inhibited by 27±2%, as compared to control cells incubated with ethanol vehicle alone. The presence of anti-TGF-beta antibody completely reversed the inhibition of proliferation due to TMX. ELISA assays for TGF-beta confirmed that medium conditioned on human EX cultures in the presence of 5 $\mu$M TMX contained 6.0±2.0 ng/ml total TGF-beta protein, of which 55±5% was activated.

The effect of heparin on proliferation of human ED and EX cultures was examined. Heparin IC86-1771, known to inhibit proliferation of rat ED VSMC by releasing a TGF-beta-like activity from serum, partially inhibited the proliferation of human EX cultures, but not ED cultures. At 100 $\mu$g/ml and at 48 h after addition, heparin inhibited the increase in cell number in EX cultures by 51±10%; at 96 h after addition, by 71±15%. In ED cultures at 96 h after addition of 100 $\mu$g/ml heparin, the increase in cell number was inhibited by 8±5%. Anti-TGF-beta antibody did not abolish the ability of heparin to inhibit the proliferation of human EX cultured VSMC. Therefore, human EX VSMC may release more TGF-beta from 20% FCS than could be neutralized by added antibody, or heparin affected TGF-beta DNA synthesis as well as TGF-beta activation at the heparin concentrations tested.

The effect of mitogens on the entry of ED and EX cells into DNA synthesis was examined. Quiescent ED and EX VSMC were restimulated with either 20% FCS or 100 ng/ml PDGF-BB in D-MEM, and entry into DNA synthesis was monitored during successive 8 h pulses using [$^3$H] thymidine. EX cells entered DNA synthesis in response to both mitogenic stimuli more rapidly than ED cells. The EX cells reached peak rate of DNA synthesis in response to FCS 16–24 h after stimulation. The ED cells reached peak rate of DNA synthesis 24–32 h after mitogenic stimulation.

Quiescent EX cells were then exposed to various mitogens, and stimulation of DNA synthesis was determined by incorporation of [$^3$H]thymidine 16–32 h after stimulation. DNA synthesis was stimulated by 20% FCS by 8.0±1.5 fold, compared to control cells that remained in serum-free D-MEM throughout. PDGF-BB and PDGF-AA caused a ≈3.0 fold stimulation of DNA synthesis. Insulin-like growth factor (IGF-1; 25 ng/ml) provided a 1.2 fold stimulation. However, epidermal growth factor (EGF; 100 ng/ml), basic fibroblast growth factor (bFGF; 100 ng/ml), TGF-beta (10 ng/ml), angiotensin II (AII; 100 nM) and endothelin-1 (ET-1; 100 nM) did not significantly stimulate DNA synthesis.

Quiescent ED cells were exposed to various mitogens, and stimulation of DNA synthesis was determined by [$^3$H] thymidine incorporation 16–40 h after stimulation. DNA synthesis was stimulated by 20% FCS by 25±6 fold, compared to control cells that remained in serum-free D-MEM throughout. PDGF-BB stimulated ≈3.0 fold, but PDGF-AA stimulated only 2.0 fold. The latter response was also variable (1 of 3 cultures did not respond to PDGF-AA), in contrast to the stimulation of EX VSMC. IGF-1 and EGF stimulated DNA synthesis 1.3 fold, and bFGF, TGF-beta, AII and ET-1 did not stimulate DNA synthesis.

EXAMPLE 4

TGF-beta and Transgenic apo(a) Mice

Apo(a) mice. Human apo(a) has been expressed in transgenic mice (*Nature* 360:670–72, 1992), a species that normally lacks apo(a). These mice were used to study whether inhibition of TGF-beta activation, resulting in enhanced VSMC proliferation, represents a key step in atherogenesis.

Apo(a) transgenic mice, when fed a lipid-rich diet, develop vascular lesions similar to the fatty streak lesions in early human atherosclerosis. Immunoperoxidase labeling showed that apo(a) accumulated in the vessel wall at strongly staining focal regions in the luminal surface of the vessel. This phenomenon was studied using the more sensitive technique of immunofluorescence labeling.

Briefly, transgenic apo(a) mice, confirmed for the presence of the apo(a) gene by Southern blotting, and normal litter mates were obtained by continued crossing of transgenic mice with C57/B16×SJL hybrids. The heart and attached aorta were dissected out, immediately frozen in liquid nitrogen, embedded, and 6 $\mu$m frozen sections were prepared. The sections were fixed in ice-cold acetone for 90 seconds and stored at −20° C. until used. All fluorescent labeling procedures were performed at 4° C. For apo(a) immunolabeling, sections were incubated with 3% BSA in Tris-buffered saline (TBS) for 30 min, then with sheep anti-human Lp(a) antibody that had been adsorbed against human plasminogen diluted 1:1000 in TBS containing 3% BSA. The anti-human Lp(a) antibody had no detectable cross-reactivity with mouse plasminogen. The bound primary antibody was detected using fluorescein-conjugated rabbit anti-sheep IgG diluted 1:80 in TBS containing 3% BSA, and visualized by fluorescence microscopy at 400× magnification ($\lambda$exc=440nm; $\lambda$em=510nm); photomicrographs were taken with 5 second exposures (ASA 1600). The tissue sections were indistinguishable whether the mice were fed a normal diet (Techlad, Madison, Wis.; 4% mouse/rat chow) or a lipid-rich diet containing 1.25% cholesterol, 7.5% saturated fat as cocoa butter, 7.5% casein and 0.5% soldium cholate.

Immunofluorescence labeling for apo(a) showed strongly labeled foci of apo(a) in the luminal surface of the aortic wall, but apo(a) was also labeled at a substantially lower intensity throughout the media of the vessel. No apo(a) labeling was detected in the aortic sections from the normal litter mate mice. The serum concentration of apo(a) in the transgenic mice was 3.8±1.2 mg/dl. Analysis of human arteries and of mice injected with radiolabeled apo(a) showed that plasma-derived apo(a) penetrates the vessel wall. In situ hybridization suggested that little, if any, apo(a) in the vessel wall of the apo(a) mice was derived from local synthesis.

Total and activated plasminogen. Activation of plasminogen in the aortic wall was assayed using the specific inhibitor, $\alpha$2-antiplasmin ($\alpha$2-AP), which forms a stable covalent conjugate with active plasmin, but does not bind covalently to plasminogen, apo(a) or other proteins in the vessel wall. Briefly, $\alpha$2-AP (Sigma) was labeled with either fluorescein isothiocyanate (Sigma) or trimethylrhodamine isothiocyanate (*Experimentia* 16:430, 1960), and separated from unincorporated label by two gel filtrations on Sephadex G25.

For determination of activated plasminogen, sections were incubated for 16 h with $\alpha$2-AP-FITC (1 $\mu$g/ml) and washed. For determination of total plasminogen, the sections were incubated with $\mu$2-AP-FITC, as above, washed thoroughly in TBS containing 0.2% Nonidet-P40 (NP-40) and 300 mM NaCl (wash buffer), and then incubated with 1 mg/ml recombinant human tissue plasminogen activator (rt-PA) in TBS for 3 h to activate the plasminogen. The sections were washed, incubated for 16 h with $\alpha$2-AP-TRITC (1 $\mu$g/ml), then washed throughly in wash buffer, followed by TBS. Bound labeled $\alpha$2-AP was visualized by fluorescence microscopy at 400× magnification ($\lambda$exc=440nm; $\lambda$em=510nm for FITC label; $\lambda$exc=490nm; $\lambda$em=580nm for TRITC label). The low level of background autofluorescence from the acetone-fixed sections was subtracted for each section from the fluorscence of the label. There were no significant differences in the autofluorescence intensity either between sections from the same mouse aorta, or between normal litter mate aortic sections and those from transgenic apo(a) mice. Photomicrographs of bound $\alpha$2-AP-FITC to detect active plasmin were exposed for 10 sec, and of bound $\alpha$2-AP-TRITC to detect plasminogen were exposed for 1 sec (1600 ASA).

Quantitation of fluorescence. A Magiscan image analysis system (Joyce-Loebl) with extended linear range TV camera (Photonic Science) attached to a Nikon Diaphor inverted fluorescence microscope was used to quantitate the fluorescence. The gain control on the photomultiplier was set so that the average pixel value over the area of the vessel wall was between 2–5% of full scale. For each section, four fields of aortic wall were selected randomly under phase contrast (400× magnification), and separate fluorescence images were captured using filters for fluorescein and trimethylrhodamine. For TGF-beta and plasminogen/plasmin, the average pixel value for the fluorescence intensity over the whole area of the vessel media was calculated, and the mean for the four sections from each mouse (i.e., 16 fields of view) was computed. For osteopontin, the vessel media was only partly labeled, and only pixels with intensity values >5% of full scale were included in the calculation of average pixel value. The number of pixels ($\times 10^{-2}$) above the threshold is shown as the area labeled for osteopontin.

The $\alpha$2-AP-FITC was detected in aortic sections of both the normal and apo(a) mice, predominantly associated with the elastic laminae of the vessels. Quantitation of the fluorescent label showed approximately 3 fold less active plasmin in the vessel wall of the apo(a) mice than in the normal mice, regardless of whether the mice had been fed a lipid-rich or normal diet, as shown in Table 1.

TABLE 1

Quantitative fluorescent data

| | Normal mice | | Transgenic apo(a) mice | |
|---|---|---|---|---|
| | Normal diet | Lipid-rich | Normal diet | Lipid-rich |
| TGF-β | | | | |
| Total | 112 ± 7 | 95 ± 12 | 115 ± 1 | 109 ± 6 |
| % active | 90 ± 6 | 90 ± 5 | 36 ± 3* | 46 ± 8* |
| Plasminogen | | | | |
| Total | 702 ± 47 | 748 ± 95 | 789 ± 121 | 688 ± 133 |
| % active | 6.3 ± 1.3 | 6.1 ± 0.6 | 1.7 ± 0.7* | 1.9 ± 1.2* |
| Osteopontin | | | | |
| Total | 1.4 ± 0.8 | 0.4 ± 0.1 | 32.3 ± 4.4* | 12.6 ± 2.1*+ |
| Area | 0.7 ± 0.9 | 1.2 ± 1.6 | 80.3 ± 0.0* | 103 ± 31.7*+ |

*p <0.05 for apo(a) mice compared with normal litter mate mice
+p <0.05 for apo(a) mice on a lipid-rich diet compared with apo(a) mice on a normal diet (Student's unpaired t-test)

Control experiments demonstrated that the α2-AP-FITC bound only to active plasmin in the sections. No fluorescence was detected in aortic sctions that were incubated with α2-AP-FITC in the presence of a large excess (1 mU) of exogenous active plasmin. Aortic sections were also incubated with α2-AP-FITC after treatment with the plasmin inhibitor, aprotinin (100 μg/ml), and no fluorescence was detected, demonstrating that there was no interaction of the label with the sections in the absence of active plasmin.

To assay for plasminogen, active plasmin was first labeled with α2-AP-FITC, as described above, then the same sections were treated with rt-PA to activate the plasminogen. The sections were relabeled for active plasminogen using α2-AP-TRITC. When the rt-PA was omitted, no further staining for active plasmin with α2-AP-TRITC was observed. Quantitation of the two fluorescent labels of active plasmin before and after activation of the plasminogen provides a measure of the total amount of plasminogen and of the proportion of plasminogen that was already activated in the sections (see Table 1). There was no significant difference in the total amounts of plasminogen in the sections from the apo(a) mice and normal mice. In the normal mice, ≈6% of the plasminogen was activated to plasmin, compared with only 2% in the apo(a) transgenic mice. Thus, apo(a) inhibits plasminogen activation.

TGF-beta. To determine whether the low plasmin concentration in the aortic wall of the apo(a) mice resulted in reduced activation of TGF-beta, immunofluorescent labels were used to quantitate active TGF-beta and total TGF-beta (active+latent). Briefly, sections prepared as described above were labeled for total TGF-beta for 2 h with 25 μg/ml of BDA47 (R&D Systems), a rabbit polyclonal antiserum to TGF-beta that detects isoforms 1 and 3 with equal sensitivity, but does not distinguish between latent and active TGF-beta. The sections were washed 3 times in TBS, and incubated with goat anti-rabbit IgG (Sigma; 1:50 dilutaion) conjugated with TRITC. Both antibodies were diluted in TBS containing 3% BSA. The same section was then washed 3 times in TBS and labeled for active TGF-beta with R2X (TGF-beta type II receptor extracellular domain, which recognizes the active form of isoforms 1 and 3 only) that was conjugated with FITC, as described above. Sections were incubated for 16 h, then washed 3 times in PBS. Bound label was visualized by fluorescence microscopy, as described above. Photomicrograph exposures were 5 sec (1600 ASA). To calibrate the fluorescence intensities of the two labels, a solution containing various proportions of active TGF-beta (6 ng/ml of total TGF-beta) was spotted on gelatin-polylysine-coated slides and allowed to dry at room temperature. The protein spots were labeled for total and active TGF-beta, as described for the aortic sections, and the fluorescence intensity ratios (TRITC/FITC) were determined. False color images of the proportion of TGF-beta in the active form were computed from the fluorescence ratios of the aortic sections using the calibration.

TGF-beta was present throughout the aortic media, predominantly associated with the elastic laminae in both the normal and apo(a) mice. No fluorescent label was bound to the sections when the primary anti-TGF-beta antibody was omitted. Quantitation of the fluorescent label showed no significant difference in the total amount of TGF-beta present in the aortic wall of normal and apo(a) mice (see Table 1).

Active TGF-beta was assayed using a truncated extracellular domain of the type II TGF-beta receptor fused to glutathione-S-transferase (R2X) that had been FITC labeled. This label was detected in sections from both normal and apo(a) mice in association with the elastic laminae. In the presence of 100 mg/ml recombinant active TGF-beta-1, the binding of R2X-FITC to the sections was completely blocked. In addition, glutathione-S-transferase labeled with FITC did not detectably bind to aortic sections from either normal or apo(a) mice.

The TGF-beta present in the aortic wall from apo(a) mice was significantly less active than the TGF-beta in the aortic wall from normal mice, irrespective of whether the mice had been fed a lipid-rich diet or normal diet (see Table 1). Thus, TGF-beta activation in the aortic wall is significantly inhibited by the presence of apo(a). Moreover, activation of TGF-beta is most strongly inhibited at the sites of highest apo(a) accumulation. Therefore, changes in the vessel wall that are a consequence of reduced TGF-beta activity will occur preferentially at the sites of focal apo(a) accumulation, but will not be dependent on the accumulation of lipid.

The mouse serum was also assayed for inhibition of TGF-beta activation by apo(a), using ELISAs for total and active TGF-beta (see Example 1). The total TGF-beta in the serum of apo(a) mice was 14.4±4.7 ng/ml; in normal mice it was 14.2±3.5 ng/ml. However, the proportion of total TGF-beta that was active in the serum of apo(a) mice was 34±19%, compared with 92±12% active TGF-beta in the serum of normal mice.

Osteopontin. Aortic sections were assayed for osteopontin, a marker of activated smooth muscle cells. Osteopontin was detected by incubating sections with monoclonal antibody MPIIIB10$_1$ (National Institute of Health Developmental Studies Hybridoma Bank) at 10 μg/ml in TBS containing 3% BSA for 16 h. The sections were washed 3 times in TBS, and bound antibody was detected using goat anti-mouse IgG conjugated to fluorescein (Sigma F-2012; 1:50 dilution; 2 h). Photomicrographs were obtained with 2.5 sec exposure time (ASA 1600).

Fluorescent labeling of osteopontin was detected in the aortic sections from apo(a) mice on either a lipid-rich or normal diet. Although a small increase in labeling for osteopontin was detected throughout the media of the aortae from transgenic apo(a) mice, very high levels of osteopontin labeling were co-localized with regions of focal apo(a) accumulation and very low TGF-beta activation. Treatment of apo(a) mice with bromodeoxyuridine for 24 h before sacrifice showed no significant mitotic activity in the aortic media. Thus, in the absence of physical injury, replication rates in atheromatous plaques are low, reflecting the slow growth of the lesions. Areas of aortic sections from normal mice that showed high proportions of active TGF-beta did not show detectable labeling for osteopontin. The total intensity and area of osteopontin labeling in the normal mouse sections were also very low compared with the apo(a) mouse sections. Therefore, the presence of apo(a) induces osteopontin expression in VSMC in the aortic wall, similar to the changes that occur during the development of vascular lesions, regardless of whether the mice are fed a lipid-rich or normal diet. Accumulation of lipid into the vessel wall under conditions where circulating lipid is elevated may be a consequence, rather than a cause, of the changes in VSMC activation marked by the expression of osteopontin. Previous studies have shown that activated VSMC in culture accumulate about 20 fold more lipid than contractile VSMC.

The results of these experiments link apo(a) to the inhibition of plasminogen and latent TGF-beta activation. The inhibition of TGF-beta activation likely contributes to the subsequent development of fatty lesions when apo(a) containing subjects (mice or human) are subject to a lipid-rich diet.

EXAMPLE 5

Tamoxifen Inhibits Migration and Lipid Uptake in Atherosclerosis

Cell culture. Rat aortic SMCs from 12–20 week old Wistar male rats were prepared by enzyme dispersion, as described in Example 1. The cultured cells were confirmed as >99% SMC by staining for SM-MHC, and proliferated with a cell cycle time of 36 h. Cells were passaged as described in Example 1, and were used either in primary culture or between passages 6–12.

Human aortic SMC from donors of either sex, aged 15–60, were prepared by explanting 1 mm$^3$ of medial tissue, as described in Example 3.

Migration. Migration was assayed using SMC grown to confluence on glass coverslips. A defined injury is performed on the confluent layer of cells, which are allowed to recover in D-MEM+10% FCS for 24 h. Bromodeoxyuridine (10 $\mu$M) is added between 18–24 h, to label proliferating cells. Cells migrating past the boundary of the wound edge at 24 h are detected by propidium iodide (PI) staining of the cell nuclei (500 $\mu$M PI in PBS+0.5% NP-40 for 30 min at room temperature). Cells that synthesized DNA were detected by antibody staining for bromodeoxyuridine using fluorescein-conjugated anti-bromodeoxyuridine antibodies. Migrating and proliferating cells in each field of view were simultaneously counted by image analysis of the rhodamine emission from PI and fluorescein emission from bromodeoxyuridine.

Lipid uptake. Cells in 24 well plastic dishes were incubated with serum-free D-MEM for 24 h or 1 h at 37° C., then washed in PBS+1% BSA at 4° C. on ice for 30 min. Cells were incubated with $^{125}$I-labeled LDL at various concentrations for 3 h in the presence or absence of cold competitor LDL. The cells were washed six times with ice-cold PBS, lysed in 0.1M NaOH or 0.1% SDS, and cell-associated counts of LDL were determined by gamma counting.

Apo(a) transgenic mice. Apo(a) [human 500 kD isoform] was expressed from the transferrin promotor in C57/B16× SJL F1 cross mice. Mice were sacrificed at 24 weeks of age after 12 weeks on a lipid-rich or normal diet. Heart/lung/aortae frozen blocks were prepared, and 6 $\mu$m frozen sections prepared on gelatin-coated slides. Sections were either fixed in acetone for 90 sec (for quantitative immunofluorescence; QIF) or in formaldehyde vapor for 18 h (for histology). Sections were stored at −20° C. until analyzed.

Histology. Sections were stained with trichrome stain or hematoxylin/eosin or oil red O/light green for lipid accumulation. Slides fixed in paraformaldehyde were rehydrated, incubated for 18 min in fresh oil red O, rinsed, and then incubated 1–2 min in fresh light green SF yellowish. The slides were then dehydrated, mounted, and the quantity and position of lipid deposition was analyzed by image analysis.

Quantitative immunofluorescence (QIF). Sections fixed in acetone were rehydrated in TBS+3% BSA for 30 min. The sections were incubated with primary antibody (anti-apo(a) immunosorbed on plasminogen, from Immunex, 1:1000 dilution; anti-total TGF-beta BDA47, from R&D Systems, 1:200 dilution; MBPIIIB10 anti-osteopontin antibody, from NIHDSHB, 1:200 dilution) in TBS+3% BSA. Sections were washed 3×3 min in PBS, then incubated with fluorescent-labeled second antibody for 2 h. After washing 3×3 min and mounting, bound fluorescence was quantitated by image analysis. Two markers could be examined on the same section using fluorescein and rhodamine as distinct fluorescent labels with different excitation and emission characteristics.

Active TGF-beta was localized and quantitated following incubation of slides with fluorescent-labeled extracellular matrix domain of the TGF-beta type II receptor (R2X), expressed in *E. coli* as a glutathione-S-transferase fusion protein.

Results. When confluent cells were injured in the presence of serum, many cells migrated into the wound area within 24 h. Proliferation was also stimulated under these conditions (7% of cells entered DNA synthesis, compared with 3% in an uninjured, control confluent culture). The addition of TGF-beta-1 (10 ng/ml) or tamoxifen (TMX; 10 $\mu$M) to rat cells at the time of wounding substantially inhibited migration (approximately 90% less cells crossed the boundary of the wound), consistent with previous data that demonstrated that TGF-beta inhibited SMC migration in Boyden Chamber assays. The inhibition of migration by TMX was reversed (>90%) by a neutralizing antibody to TGF-beta-1 (25 $\mu$g/ml).

In contrast, TGF-beta and TMX did not significantly inhibit the entry into DNA synthesis that was stimulated upon wounding. This observation is consistent with previous data that showed that TGF-beta and TMX slow SMC proliferation by extending the cell cycle in the $G_2$ phase, rather than by inhibiting or slowing entry into DNA synthesis.

These data agree with previous work that showed that apo(a) inhibits TGF-beta activation in culture, thereby promoting SMC migration. As described in Example 4, apo(a) stimulated VSMC proliferation. Apo(a) is associated with atherogenesis in man and in apo(a) transgenic mice. When apo(a) accumulates in conjunction with reduced levels of active TGF-beta, both migration and proliferation will increase. TMX, which stimulates formation of active TGF-beta, should ameliorate atherogenesis, regardless of whether migration or proliferation (or both) play key roles in pathogenesis.

In adult rat aorta SMC, LDL accumulation is very low, both in freshly dispersed cell preparations and in primary and secondary cultures. This phenomenon is due to very low levels of LDL receptors (200–400 receptors/cell), irrespective of whether the cells were exposed to lipoproteins.

In contrast, intimal SMC derived from rats 14 days after balloon injury to the carotid artery have a greater (≈5 fold) uptake of LDL, due to increased LDL receptor numbers (1500–2000 receptors/cell). When intimal cells or neonatal cells (displaying very similar properties) are treated with 10 ng/ml TGF-beta for 48 h, these cells modulate, apparently irreversibly, to the adult phenotype. This phenotypic modulation is accompanied by a down-regulation of LDL receptors (≈800 receptors/cell), with a reduction of LDL uptake of >80%. The presence of TGF-beta may therefore reduce lipid accumulation by SMC.

The data obtained with apo(a) transgenic mice are consistent with this prediction. In these mice, apo(a) is accumulated at high levels at the intimal surface of the aorta. TGF-beta activation is strongly down-regulated from >80% in control aortas to <20% in apo(a) aortas. Lipid accumulation occured at these sites in transgenic mice that were fed a lipid-rich diet and had elevated circulating LDL levels. Thus, reduced TGF-beta activity correlates with increased SMC accumulation of LDL from the circulation. TMX, which is capable of elevating TGF-beta in vivo, may inhibit lipid accumulation in vivo.

These data suggest the following conclusions:

a. Atherosclerosis results from at least five processes (migration; lipid accumulation; ECM formation; inflammation; proliferation). The relative contribution of each process, and of their interactions, is not clear.

b. TMX and TGF-beta should reduce or inhibit migration and lipid accumulation by SMC.

c. TMX and TGF-beta should stimulate ECM production.

d. TMX and TGF-beta should decrease SMC proliferation.

e. All of these noted effects should contribute to some degree to the predicted beneficial effects of TMX on atherosclerosis and its progression of clinical significance and myocardial infarction.

While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. A method for preventing atherosclerosis in a mammal at risk therefor, or treating atherosclerosis in a mammal, which method comprises orally administering to the mammal the following:

a dose of a therapeutic agent in an amount effective when administered orally to elevate the level of TGF-beta, wherein the increase in TGF-beta inhibits atherosclerotic lesion formation or development in the mammal.

2. The method of claim 1 wherein a series of doses are administered.

3. The method of claim 1 wherein the therapeutic agent inhibits lipid accumulation by the vessel.

4. The method of claim 1 wherein the therapeutic agent comprises trans-2-[4-(1,2-diphenyl-1-butenyl)phenoxy]-N,N-dimethyl-ethylamine, or a structural analog thereof.

5. The method of claim 4 wherein the therapeutic agent comprises a structural analog of trans-2-[4-(1,2-diphenyl-1-butenyl)phenoxy]-N,N-dimethyl-ethylamine.

6. The method of claim 1 wherein the therapeutic agent stabilizes atherosclerotic plaque.

7. The method of claim 1 wherein the therapeutic agent stimulates the production of TGF-beta mRNA or the expression of TGF-beta.

8. The method of claim 1 wherein the therapeutic agent cleaves the propeptide form of TGF-beta.

9. A therapeutic method comprising orally administering to a mammal an amount of a therapeutic agent effective upon oral administration to elevate the level of TGF-beta so as to treat a diseased blood vessel in said mammal, wherein said disease is associated with the diminution in the lumen volume of the diseased vessel, and wherein the therapeutic agent stabilizes atherosclerotic plaque, inhibits lipid accumulation, or inhibits or reduces diminution in vessel lumen diameter in the diseased vessel.

10. The method of claim 9 wherein a series of doses is administered over time to the mammal.

11. The method of claim 9 wherein the therapeutic agent comprises trans-2-[4-(1,2-diphenyl-1-butenyl)phenoxy]-N,N-dimethyl-ethylamine, or a structural analog thereof.

12. The method of claim 9 wherein the therapeutic agent stimulates the production of TGF-beta mRNA or the expression of TGF-beta.

13. The method of claim 9 wherein the therapeutic agent cleaves the propeptide form of the TGF-beta.

14. The method of claim 1 or 9 wherein the therapeutic agent increases the bioavailability of TGF-beta.

15. The method of claim 1 or 9 wherein the administration increases the level of active TGF-beta in said mammal relative to the level of active TGF-beta in said mammal prior to said administration.

16. The method of claim 1 or 9 wherein the administration increases the level of latent TGF-beta in said mammal relative to the level of latent TGF-beta in said mammal prior to said administration.

* * * * *

UNITED STATES PATENT AND TRADEMARK OFFICE
CERTIFICATE OF CORRECTION

PATENT NO. : 5,847,007
DATED : December 8, 1998
INVENTOR(S) : Grainger et al.

It is certified that error appears in the above-identified patent and that said Letters Patent is hereby corrected as shown below:

Application No.
Item [21], delete "242,161" and insert -- 08/242,161 --, therefor.

Column 1,
Line 7, before "Ser. No." add -- U.S. Serial No. 08/300,357, filed September 2, 1994, now issued as U.S. Patent No. 5,472,985, which is a continuation of --.

Column 3,
Lines 47-48, delete "heparin, angiotensin II,".

Signed and Sealed this

Sixth Day of November, 2001

Attest:

NICHOLAS P. GODICI
Attesting Officer    Acting Director of the United States Patent and Trademark Office